(12) United States Patent
Rodrigues et al.

(10) Patent No.: US 11,944,344 B2
(45) Date of Patent: Apr. 2, 2024

(54) GUIDANCE SYSTEM, METHOD AND DEVICES THEREOF

(71) Applicant: KARL STORZ SE & Co. KG, Tuttlingen (DE)

(72) Inventors: Pedro Rodrigues, Braga (PT); João Luis Araújo Martins Vilaça, Vila Frescainha S. Martinho (PT); Jorge Correia Pinto, Oporto (PT); Jaime Francisco Cruz Fonseca, Braga (PT); Estevão Lima, Oporto (PT)

(73) Assignee: KARL STORZ SE & Co. KG, Tuttlingen (DE)

( * ) Notice: Subject to any disclaimer, the term of this patent is extended or adjusted under 35 U.S.C. 154(b) by 623 days.

(21) Appl. No.: 17/032,333

(22) Filed: Sep. 25, 2020

(65) Prior Publication Data
US 2021/0007774 A1 Jan. 14, 2021

Related U.S. Application Data

(63) Continuation of application No. PCT/IB2019/053083, filed on Apr. 15, 2019.

(30) Foreign Application Priority Data

Apr. 13, 2018 (PT) .......................... 110686

(51) Int. Cl.
*A61B 17/34* (2006.01)
*A61B 34/00* (2016.01)
(Continued)

(52) U.S. Cl.
CPC .......... *A61B 17/3403* (2013.01); *A61B 34/76* (2016.02); *A61B 90/37* (2016.02);
(Continued)

(58) Field of Classification Search
CPC ...... A61B 17/3403; A61B 2017/00115; A61B 2034/107; A61B 2034/2051;
(Continued)

(56) References Cited

U.S. PATENT DOCUMENTS

| | | |
|---|---|---|
| 6,171,303 B1 | 1/2001 | Ben-Haim et al. |
| 6,395,016 B1 | 5/2002 | Oron et al. |

(Continued)

FOREIGN PATENT DOCUMENTS

| | | |
|---|---|---|
| AU | 2006202149 B2 | 3/2009 |
| AU | 2017272200 A1 | 1/2018 |

(Continued)

OTHER PUBLICATIONS

International Preliminary Report on Patentability for International Application No. PCT/IB2019/053083, dated Oct. 22, 2020.
(Continued)

*Primary Examiner* — Michael T Rozanski
(74) *Attorney, Agent, or Firm* — Jason H. Vick; Sheridan Ross, PC

(57) ABSTRACT

A guidance system, a method and a device for dynamically guiding a surgical needle catheter onto an organ to be surgically operated of a patient. In particular, the disclosure relates to a guidance system, a method and a device to aid in the percutaneous kidney puncture.

30 Claims, 11 Drawing Sheets

(51) Int. Cl.
*A61B 90/00* (2016.01)
*A61B 90/92* (2016.01)
*A61B 34/10* (2016.01)
*A61B 34/20* (2016.01)
*A61M 25/01* (2006.01)

(52) U.S. Cl.
CPC ........ *A61B 90/92* (2016.02); *A61B 2034/107* (2016.02); *A61B 2034/2051* (2016.02); *A61M 25/0127* (2013.01)

(58) Field of Classification Search
CPC . A61B 2090/0807; A61B 34/25; A61B 34/76; A61B 90/37; A61B 90/92; A61M 25/0127
See application file for complete search history.

(56) References Cited

U.S. PATENT DOCUMENTS

| | | | |
|---|---|---|---|
| 6,436,095 B1 | 8/2002 | Ben-Haim et al. | |
| 6,447,504 B1 | 9/2002 | Ben-Haim et al. | |
| 6,542,766 B2 | 4/2003 | Hall et al. | |
| 6,574,492 B1 | 6/2003 | Ben-Haim et al. | |
| 6,600,948 B2 | 6/2003 | Ben-Haim et al. | |
| 6,843,793 B2 | 1/2005 | Brock et al. | |
| 6,860,878 B2 | 3/2005 | Brock | |
| 6,915,149 B2 | 6/2005 | Ben-Haim et al. | |
| 6,949,106 B2 | 9/2005 | Brock et al. | |
| 7,051,738 B2 | 5/2006 | Oron et al. | |
| 7,090,683 B2 | 8/2006 | Brock et al. | |
| 7,114,500 B2 | 10/2006 | Bonutti | |
| 7,169,141 B2 | 1/2007 | Brock et al. | |
| 7,214,230 B2 | 5/2007 | Brock et al. | |
| 7,297,142 B2 | 11/2007 | Brock | |
| 7,371,210 B2 | 5/2008 | Brock et al. | |
| 7,604,642 B2 | 10/2009 | Brock | |
| 7,653,427 B2 | 1/2010 | Essner et al. | |
| 7,708,741 B1 | 5/2010 | Bonutti | |
| 7,713,190 B2 | 5/2010 | Brock et al. | |
| 7,744,622 B2 | 6/2010 | Brock et al. | |
| 7,750,311 B2 | 7/2010 | Daghighian et al. | |
| 7,758,569 B2 | 7/2010 | Brock | |
| 7,775,972 B2 | 8/2010 | Brock et al. | |
| 7,789,875 B2 | 9/2010 | Brock et al. | |
| 7,835,784 B2 | 11/2010 | Mire et al. | |
| 7,867,241 B2 | 1/2011 | Brock et al. | |
| 7,905,828 B2 | 3/2011 | Brock et al. | |
| 7,918,861 B2 | 4/2011 | Brock et al. | |
| 7,931,586 B2 | 4/2011 | Brock et al. | |
| 8,050,743 B2 | 11/2011 | Daghighian et al. | |
| 8,068,896 B2 | 11/2011 | Daghighian et al. | |
| 8,086,298 B2 | 12/2011 | Whitmore, III et al. | |
| 8,114,097 B2 | 2/2012 | Brock et al. | |
| 8,190,238 B2 | 5/2012 | Moll et al. | |
| 8,204,575 B2 | 6/2012 | Stetz et al. | |
| 8,257,303 B2 | 9/2012 | Moll et al. | |
| 8,303,576 B2 | 11/2012 | Brock | |
| 8,311,611 B2 | 11/2012 | Csavoy et al. | |
| 8,401,617 B2 | 3/2013 | Whitmore, III et al. | |
| 8,414,472 B2 | 4/2013 | Hagelauer | |
| 8,414,598 B2 | 4/2013 | Brock et al. | |
| 8,467,851 B2 | 6/2013 | Mire et al. | |
| 8,498,691 B2 | 7/2013 | Moll et al. | |
| 8,504,139 B2 | 8/2013 | Jacobsen et al. | |
| 8,617,102 B2 | 12/2013 | Moll et al. | |
| 8,623,030 B2 | 1/2014 | Bonutti | |
| 8,641,726 B2 | 2/2014 | Bonutt | |
| 8,688,196 B2 | 4/2014 | Whitmore, III et al. | |
| 8,709,034 B2 | 4/2014 | Keast et al. | |
| 8,801,661 B2 | 8/2014 | Moll et al. | |
| 8,814,874 B2 | 8/2014 | Hunter et al. | |
| 8,834,490 B2 | 9/2014 | Bonutti | |
| 8,840,629 B2 | 9/2014 | Bonutti | |
| 8,858,557 B2 | 10/2014 | Bonutti | |
| 8,880,158 B2 | 11/2014 | Spector | |
| 8,932,316 B2 | 1/2015 | Keast et al. | |
| 9,033,893 B2 | 3/2015 | Spector | |
| 9,060,797 B2 | 6/2015 | Bonutti | |
| 9,078,685 B2 | 7/2015 | Smith et al. | |
| 9,226,688 B2 | 1/2016 | Jacobsen et al. | |
| 9,226,800 B2 | 1/2016 | Burg et al. | |
| 9,232,985 B2 | 1/2016 | Jacobsen et al. | |
| 9,254,093 B2 | 2/2016 | Spector | |
| 9,259,290 B2 | 2/2016 | Jenkins et al. | |
| 9,282,908 B2 | 3/2016 | Spector | |
| 9,345,532 B2 | 3/2016 | Laufer | |
| 9,345,875 B2 | 5/2016 | Appenrodt et al. | |
| 9,421,070 B2 | 8/2016 | Keast et al. | |
| 9,439,581 B2 | 9/2016 | Dinsmoor et al. | |
| 9,439,653 B2 | 9/2016 | Avneri et al. | |
| 9,439,735 B2 | 9/2016 | Guttman et al. | |
| 9,456,766 B2 | 10/2016 | Cox et al. | |
| 9,457,168 B2 | 10/2016 | Moll et al. | |
| 9,480,415 B2 | 11/2016 | Wald et al. | |
| 9,486,229 B2 | 11/2016 | Laufer | |
| 9,492,623 B2 | 11/2016 | Kapadia et al. | |
| 9,498,584 B2 | 11/2016 | Kapadia et al. | |
| 9,498,585 B2 | 11/2016 | Kapadia et al. | |
| 9,521,961 B2 | 12/2016 | Silverstein et al. | |
| 9,681,919 B2 | 6/2017 | Glossop | |
| 9,554,716 B2 | 7/2017 | Burnside et al. | |
| 9,693,699 B2 | 7/2017 | Spector et al. | |
| 9,706,935 B2 | 7/2017 | Spector | |
| 9,737,232 B2 | 8/2017 | Fan | |
| 9,782,229 B2 | 10/2017 | Crawford et al. | |
| 9,861,836 B2 | 1/2018 | Schwartz | |
| 9,993,306 B2 | 6/2018 | Keast et al. | |
| 2002/0087048 A1 | 7/2002 | Brock et al. | |
| 2002/0087148 A1 | 7/2002 | Brock et al. | |
| 2002/0095175 A1 | 7/2002 | Brock et al. | |
| 2002/0120252 A1 | 8/2002 | Brock et al. | |
| 2002/0128661 A1 | 9/2002 | Brock et al. | |
| 2002/0128662 A1 | 9/2002 | Brock et al. | |
| 2002/0138082 A1 | 9/2002 | Brock et al. | |
| 2005/0288576 A1 | 12/2005 | Fegert et al. | |
| 2006/0176242 A1* | 8/2006 | Jaramaz | G02B 27/017 345/7 |
| 2007/0232896 A1 | 10/2007 | Gilboa et al. | |
| 2008/0119872 A1 | 5/2008 | Brock et al. | |
| 2008/0125793 A1 | 5/2008 | Brock et al. | |
| 2008/0132913 A1 | 6/2008 | Brock et al. | |
| 2008/0177285 A1 | 7/2008 | Brock et al. | |
| 2009/0114039 A1 | 5/2009 | Schultze et al. | |
| 2010/0010343 A1 | 1/2010 | Daghighian et al. | |
| 2010/0094116 A1 | 4/2010 | Silverstein | |
| 2010/0312094 A1 | 12/2010 | Guttman et al. | |
| 2011/0237935 A1* | 9/2011 | Kalpin | A61B 34/20 600/424 |
| 2011/0238083 A1 | 9/2011 | Moll et al. | |
| 2012/0253200 A1 | 10/2012 | Stolka et al. | |
| 2012/0289815 A1 | 11/2012 | Keast et al. | |
| 2013/0016185 A1 | 1/2013 | Stolka et al. | |
| 2013/0253599 A1 | 9/2013 | Gorek et al. | |
| 2013/0281787 A1 | 10/2013 | Avneri et al. | |
| 2014/0031674 A1 | 1/2014 | Newman et al. | |
| 2014/0046261 A1 | 2/2014 | Newman et al. | |
| 2014/0051985 A1 | 2/2014 | Fan et al. | |
| 2014/0107475 A1 | 4/2014 | Cox et al. | |
| 2014/0200639 A1 | 7/2014 | De La Rama | |
| 2014/0309560 A1 | 10/2014 | Bonutti | |
| 2014/0378999 A1 | 12/2014 | Crawford et al. | |
| 2015/0032164 A1 | 1/2015 | Crawford et al. | |
| 2015/0209119 A1 | 7/2015 | Theodore et al. | |
| 2015/0297114 A1 | 10/2015 | Cox et al. | |
| 2015/0305650 A1 | 10/2015 | Hunter et al. | |
| 2015/0335386 A1 | 11/2015 | Smith et al. | |
| 2016/0120609 A1 | 5/2016 | Jacobsen et al. | |
| 2016/0213916 A1 | 7/2016 | De La Rama | |
| 2016/0220320 A1 | 8/2016 | Crawford et al. | |
| 2016/0235493 A1 | 8/2016 | LeBoeuf, II et al. | |
| 2016/0242849 A9 | 8/2016 | Crawford et al. | |
| 2016/0242855 A1 | 8/2016 | Fichtinger et al. | |
| 2016/0256225 A1 | 9/2016 | Crawford et al. | |
| 2016/0256230 A1 | 9/2016 | Kowshik et al. | |
| 2016/0331479 A1 | 11/2016 | Crawford et al. | |

(56) References Cited

U.S. PATENT DOCUMENTS

| | | |
|---|---|---|
| 2017/0007334 A1 | 1/2017 | Crawford et al. |
| 2017/0020561 A1 | 1/2017 | Cox et al. |
| 2017/0020630 A1 | 1/2017 | Johnson et al. |
| 2017/0042621 A1 | 2/2017 | Wald et al. |
| 2017/0049991 A1 | 2/2017 | Avneri et al. |
| 2017/0071691 A1 | 3/2017 | Crawford et al. |
| 2017/0079681 A1 | 3/2017 | Burnside et al. |
| 2017/0079727 A1 | 3/2017 | Crawford et al. |
| 2017/0119339 A1 | 5/2017 | Johnson et al. |
| 2017/0172669 A1 | 6/2017 | Berkowitz et al. |
| 2017/0196590 A1 | 7/2017 | Sperry et al. |
| 2017/0231702 A1 | 8/2017 | Crawford et al. |
| 2017/0239002 A1 | 8/2017 | Crawford et al. |
| 2017/0239003 A1 | 8/2017 | Crawford et al. |
| 2017/0239006 A1 | 8/2017 | Crawford et al. |
| 2017/0239007 A1 | 8/2017 | Crawford et al. |
| 2017/0245944 A1 | 8/2017 | Crawford et al. |
| 2017/0245951 A1 | 8/2017 | Crawford et al. |
| 2017/0252112 A1 | 9/2017 | Crawford et al. |
| 2017/0258533 A1 | 9/2017 | Crawford et al. |
| 2017/0265949 A1 | 9/2017 | Crawford et al. |
| 2017/0281145 A1 | 10/2017 | Crawford et al. |
| 2017/0304013 A1 | 10/2017 | Crawford et al. |
| 2017/0311838 A1 | 11/2017 | Fan |
| 2017/0325896 A1 | 11/2017 | Donhowe et al. |
| 2017/0348061 A1 | 12/2017 | Joshi et al. |
| 2017/0360517 A1 | 12/2017 | Crawford et al. |
| 2017/0367603 A1 | 12/2017 | Spector |
| 2018/0000546 A1 | 1/2018 | Crawford et al. |
| 2018/0056040 A1 | 3/2018 | Fenech et al. |
| 2018/0062071 A1 | 3/2018 | Bolognia et al. |
| 2018/0200015 A1 | 7/2018 | Ng et al. |

FOREIGN PATENT DOCUMENTS

| | | |
|---|---|---|
| CA | 2942656 A1 | 11/2011 |
| CN | 105796177 A | 7/2016 |
| CN | 108524003 A | 9/2018 |
| EP | 1224918 A2 | 7/2002 |
| EP | 1224919 A2 | 7/2002 |
| EP | 1382293 A2 | 1/2004 |
| EP | 1428472 A2 | 6/2004 |
| EP | 2085026 A1 | 8/2009 |
| EP | 2258335 A1 | 12/2010 |
| EP | 2380550 A2 | 10/2011 |
| EP | 2912999 A1 | 9/2015 |
| EP | 2913000 A2 | 9/2015 |
| EP | 2967411 A1 | 1/2016 |
| EP | 3249427 A1 | 11/2017 |
| EP | 3278758 A2 | 2/2018 |
| EP | 3295887 A1 | 3/2018 |
| EP | 3306567 A1 | 4/2018 |
| EP | 3308824 A1 | 4/2018 |
| EP | 3318213 A1 | 5/2018 |
| EP | 3320874 A1 | 5/2018 |
| EP | 3332706 A1 | 6/2018 |
| EP | 3369394 A2 | 9/2018 |
| JP | 2009-045454 A | 3/2009 |
| JP | 5380410 B2 | 1/2014 |
| JP | 2016-512457 A | 4/2016 |
| JP | 2016-104192 A | 6/2016 |
| JP | 2017-077479 A | 4/2017 |
| JP | 2017-223657 A | 12/2017 |
| JP | 2018-011938 A | 1/2018 |
| JP | 2018-047353 A | 3/2018 |
| JP | 2018-051306 A | 4/2018 |
| JP | 2018-079304 A | 5/2018 |
| JP | 2018-094404 A | 6/2018 |
| JP | 2018-108344 A | 7/2018 |
| JP | 2018-110841 A | 7/2018 |
| JP | 2018-143766 A | 9/2018 |
| WO | WO 97/24981 | 7/1997 |
| WO | WO 97/24983 | 7/1997 |
| WO | WO 97/25101 | 7/1997 |
| WO | WO 97/29679 | 8/1997 |
| WO | WO 98/04321 | 2/1998 |
| WO | WO 98/30144 | 7/1998 |
| WO | WO 99/04706 | 2/1999 |
| WO | WO 00/16684 | 3/2000 |
| WO | WO 00/67640 | 11/2000 |
| WO | WO 00/69353 | 11/2000 |
| WO | WO 02/15973 | 2/2002 |
| WO | WO 02/051329 | 7/2002 |
| WO | WO 02/062265 | 8/2002 |
| WO | WO 03/103492 | 12/2003 |
| WO | WO 2006/027599 | 3/2006 |
| WO | WO 2007/005976 | 1/2007 |
| WO | WO 2007/038135 | 4/2007 |
| WO | WO 2007/121139 | 4/2007 |
| WO | WO 2007/048515 | 5/2007 |
| WO | WO 2007/136784 | 11/2007 |
| WO | WO 2008/028149 | 3/2008 |
| WO | WO 2009/020764 | 2/2009 |
| WO | WO 2010/036725 | 4/2010 |
| WO | WO 2010/104850 | 9/2010 |
| WO | WO 2010/144402 | 12/2010 |
| WO | WO 2010/144405 | 12/2010 |
| WO | WO 2010/144419 | 12/2010 |
| WO | WO 2011/063266 | 5/2011 |
| WO | WO 2011/137301 | 11/2011 |
| WO | WO 2011/150358 | 12/2011 |
| WO | WO 2011/150376 | 12/2011 |
| WO | WO 2012/088535 A1 | 6/2012 |
| WO | WO 2012/109760 | 8/2012 |
| WO | WO 2012/158500 | 11/2012 |
| WO | WO 2013/142386 | 9/2013 |
| WO | WO 2013/192598 | 12/2013 |
| WO | WO 2014/066383 | 5/2014 |
| WO | WO 2014/066389 | 5/2014 |
| WO | WO 2014/066397 | 5/2014 |
| WO | WO 2014/113577 | 7/2014 |
| WO | WO 2014/113612 | 7/2014 |
| WO | WO 2014/116853 | 7/2014 |
| WO | WO 2014/116961 | 7/2014 |
| WO | WO 2014/14338 | 9/2014 |
| WO | WO 2014/149183 | 9/2014 |
| WO | WO 2014/176072 | 10/2014 |
| WO | WO 2015/061674 | 4/2015 |
| WO | WO 2016/007717 | 1/2016 |
| WO | WO 2016/077419 | 5/2016 |
| WO | WO 2016/118744 | 7/2016 |
| WO | WO 2017/120434 | 7/2017 |
| WO | WO 2018/009841 | 1/2018 |
| WO | WO 2018/055433 | 3/2018 |

OTHER PUBLICATIONS

Banovac, Filip et al., "Needle Biopsy of Anatomically Unfavorable Liver Lesions with an Electromagnetic Navigation Assist Device in a Computed Tomography Environment" Journal of vascular and interventional radiology, vol. 17, pp. 1671-1675, 2006.

Bosnjak, Antonio et al. "An Electromagnetic Tracking System for Surgical Navigation with Registration of Fiducial Markers Using the Iterative Closest Point Algorithm" 10th IEEE International Conference on, Nov. 2010, pp. 1-5.

Dobrzynski, Michal Karol "Quantifying Information Transfer Through a Head-Attached Vibrotactile Display: Principles for Design and Control" IEEE Transactions on Biomedical Engineering, vol. 59, No. 7, Jul. 2012.

Fischer, Gregor S et al. "Electromagnetic Tracker Measurement Error Simulation and Tool Design" Medical Image Computing and Computer-Assisted Intervention—MICCAI 2005, ed: Springer, 2005, pp. 73-80.

Gardner, William G. "3-D Audio Using Loudspeakers" Massachusetts Institute of Technology; Sep. 1997.

Huber, Johannes et al.: Abstract for "Navigated Renal Access Using Electromagnetic Tracking: An Initial Experience" Surgical Endoscopy and Other Interventional Techniques, vol. 25, pp. 1307-1312, Apr. 2011.

Krücker, Jochen et al. "An Electro-Magnetically Tracked Laparoscopic Ultrasound for Multi-Modality Minimally Invasive Surgery" International Congress Series 1281, May 2005, pp. 746-751.

(56) References Cited

OTHER PUBLICATIONS

Levy, Elliot et al.: Abstract for "Electromagnetic Tracking-Guided Percutaneous Intrahepatic Portosystemic Shunt Creation in a Swine Model" Journal of Vascular and Interventional Radiology, vol. 18, pp. 303-307, Feb. 2007.

Meyer, Bernhard C et al. "Electromagnetic Field-Based Navigation for Percutaneous Punctures on C-arm CT: Experimental Evaluation and Clinical Application" European Radiology; vol. 18: 2855-2864; Jul. 2008.

Nagel, Markus et al. "Electromagnetic Tracking System for Minimal Invasive Interventions Using a C-arm System with CT Option: First Clinical Results" Medical Imaging 2008: Visualization, Image-Guided Procedures, and Modeling, Pts 1 and 2, vol. 6918, pp. G9180-G9180 423, 2008.

Nixon, Mark A. et al. "The Effects of Metals and Interfering Fields on Electromagnetic Trackers" Presence: Teleoperators and Virtual Environments, vol. 7, No. 2, pp. 204-218, Apr. 1998.

NDI "Aurora Features" available at http://www.ndigital.com/medical/products/aurora/; printed Sep. 24, 2020.

Wegner, Kristen "Surgical Navigation System and Method Using Audio Feedback" ICAD' 98' 1998.

Yaniv, Ziv et al. "Electromagnetic Tracking in the Clinical Environment" Technical Report; CAIMR TR-2008-1; Jul. 2008.

Wikipedia "Bombsight" retrieved from the Internet: https://en.wikipedia.org/w/index.php?title=Bombsight&oldid=826788111; Feb. 21, 2018.

International Search Report for International Application No. PCT/IB2019/053083, dated Jul. 24, 2019.

Written Opinion for International Application No. PCT/IB2019/053083, dated Jul. 24, 2019.

Examination Report for corresponding Indian Patent Application No. 202017044026, dated Jul. 5, 2022.

First Office Action (Including Translation) for corresponding Chinese Patent Application No. 201980024968.9, dated Dec. 9, 2023.

\* cited by examiner

| Planning | | | | | | | |
|---|---|---|---|---|---|---|---|
| | 3D | NeedleView | Audio | Vibration | 3D + NeedleView | 3D + NeedleView + Audio | 3D + NeedleView + Vibration |
| 3D | | ↑ | ←**** | ←** | ↑ | ↑ | ↑ |
| NeedleView | | | ←**** | ←**** | ← | ← | ← |
| Audio | | | | ↑* | ↑**** | ↑**** | ↑**** |
| Vibration | | | | | ↑**** | ↑**** | ↑**** |
| 3D + NeedleView | | | | | | ↑ | ↑ |
| 3D + NeedleView + Audio | | | | | | | ← |

| Puncturing | | | | | | | |
|---|---|---|---|---|---|---|---|
| | 3D | NeedleView | Audio | Vibration | 3D + NeedleView | 3D + NeedleView + Audio | 3D + NeedleView + Vibration |
| 3D | | ↑**** | ↑ | ↑ | ↑**** | ↑**** | ↑**** |
| NeedleView | | | ←**** | ←** | ← | ← | ↑ |
| Audio | | | | ↑ | ↑**** | ↑**** | ↑**** |
| Vibration | | | | | ↑* | ↑* | ↑** |
| 3D + NeedleView | | | | | | ← | ↑ |
| 3D + NeedleView + Audio | | | | | | | ↑ |

Fig. 12

GUIDANCE SYSTEM, METHOD AND DEVICES THEREOF

CROSS-REFERENCE TO RELATED APPLICATIONS

This application is a Continuation of International Patent Application No. PCT/IB2019/053083, filed 15 Apr. 2019, which claims priority to Portuguese Patent Application No. 110686, filed 13 Apr. 2018, each of which are incorporated herein by reference in their entirety.

TECHNICAL FIELD

One exemplary aspect of the present disclosure relates to a guidance system, a method and a device for dynamically guiding a surgical needle catheter or other medical device or instrument onto an organ or other body part of a patient for a surgical operation. In particular, one aspect of the disclosure relates to a guidance system, method and device to aid percutaneous kidney puncture.

BACKGROUND

References

Document US2014/0051985 A1 discloses a target finding system identifies a surgical target such as a kidney stone by disposing an emitter such as a magnetic source behind or adjacent the surgical target and employing a circuit to identify an axis to the emitter, thus defining an axis or path to the surgical target. Document WO 03/103492 A1 relates to a device for localizing an instrument or device, comprising at least one rotatable magnet producing a magnetic moment perpendicular to the axis of the device independently from said instrument or device.

Document WO 2017/120434 A1 relates to devices for guiding an instrument into a body of a patient, at a targeted point of entry and along an insertion path at a targeted insertion angle, are described herein, such as a guide for an access needle in a PCNL procedure for accessing the kidney to remove kidney stones, the devices comprising a base component, a guide assembly, and optionally an insertion mechanism. Document EP 2967411 A1 relates a surgical locator circuit identifies a surgical target such as a kidney stone by disposing an emitter such as a magnetic source behind or adjacent the surgical target and employing the circuit to identify an axis to the emitter, thus defining an axis or path to the surgical target.

These facts are disclosed in order to illustrate the technical problem addressed by the present disclosure. All references are herewith incorporated by reference herein in their entirety.

Additional References

[1] Z. Yaniv, E. Wilson, D. Lindisch, and K. Cleary, "Electromagnetic tracking in the clinical environment," Medical Physics, vol. 36, pp. 876-892, March 2009.
[2] N. D. Inc. Available: http://www.ndigital.com/medical/products/aurora/
[3] B. C. Meyer, O. Peter, M. Nagel, M. Hoheisel, B. B. Frericks, K. J. Wolf, et al., "Electromagnetic field-based navigation for percutaneous punctures on C-arm CT: experimental evaluation and clinical application," European Radiology, vol. 18, pp. 2855-2864, December 2008.
[4] J. Huber, I. Wegner, H. P. Meinzer, P. Hallscheidt, B. Hadaschik, S. Pahernik, et al., "Navigated renal access using electromagnetic tracking: an initial experience," Surgical Endoscopy and Other Interventional Techniques, vol. 25, pp. 1307-1312, April 2011.
[5] J. Krücker, A. Viswanathan, J. Borgert, N. Glossop, Y. Yang, and B. J. Wood, "An electro-magnetically tracked laparoscopic ultrasound for multi-modality minimally invasive surgery," in International Congress Series, 2005, pp. 746-751.
[6] M. A. Nixon, B. C. McCallum, W. R. Fright, and N. B. Price, "The effects of metals and interfering fields on electromagnetic trackers," Presence: Teleoperators and Virtual Environments, vol. 7, pp. 204-218, 1998.
[7] G. S. Fischer and R. H. Taylor, "Electromagnetic tracker measurement error simulation and tool design," in Medical Image Computing and Computer-Assisted Intervention—MICCAI 2005, ed: Springer, 2005, pp. 73-80.
[8] A. Bosnjak, G. Montilla, R. Villegas, and I. Jara, "An Electromagnetic Tracking System for Surgical Navigation with registration of fiducial markers using the iterative closest point algorithm," in Information Technology and Applications in Biomedicine (ITAB), 2010 10th IEEE International Conference on, 2010, pp. 1-5.
[9] F. Banovac, E. Wilson, H. Zhang, and K. Cleary, "Needle biopsy of anatomically unfavorable liver lesions with an electromagnetic navigation assist device in a computed tomography environment," Journal of vascular and interventional radiology, vol. 17, pp. 1671-1675, 2006.
[10] E. B. Levy, H. Zhang, D. Lindisch, B. J. Wood, and K. Cleary, "Electromagnetic tracking-guided percutaneous intrahepatic portosystemic shunt creation in a swine model," Journal of Vascular and Interventional Radiology, vol. 18, pp. 303-307, February 2007.
[11] M. Nagel, M. Hoheisel, U. Bill, K. Klingenbeck-Regn, W. A. Kalender, and R. Petzold, "Electromagnetic tracking system for minimal invasive interventions using a C-arm system with CT option: First clinical results—art. no. 69180G," Medical Imaging 2008: Visualization, Image-Guided Procedures, and Modeling, Pts 1 and 2, vol. 6918, pp. G9180-G9180 423, 2008.
[12] C. M. Wegner and D. B. Karron, "Surgical navigation system and method using audio feedback," ed: Google Patents, 2000.
[13] W. G. Gardner, 3-*D audio using loudspeakers*: Springer Science & Business Media, 1998.
[14] M. K. Dobrzynski, S. Mejri, S. Wischmann, and D. Floreano, "Quantifying information transfer through a head-attached vibrotactile display: principles for design and control," *Biomedical Engineering, IEEE Transactions on*, vol. 59, pp. 2011-2018, 2012.

GENERAL DESCRIPTION

One aspect of the present disclosure relates to a guidance system for dynamically guiding a medical device or instrument such as a surgical needle catheter onto an organ to be surgically operated of a patient, comprising:
  an EM, electromagnetic, catheter for inserting into the patient for defining the desired location to be reached by the needle catheter;
  an EM, electromagnetic, tracker of the surgical catheter location and orientation;
  a display of a 2D concentric ring target;

wherein said target being on a plane intersecting the tip of the EM catheter and perpendicular with the surgical catheter orientation;

continuously displaying a projection of a line concurrent with the needle catheter onto said target plane;

continuously displaying a plurality of concentric rings centred around the tip of the EM catheter.

One aspect of the present disclosure also relates to a guidance system, method and device to aid the percutaneous kidney puncture.

In an embodiment, the guidance system may further comprise an inner ring corresponding to a predetermined surgically acceptable region for the catheter.

In an embodiment, the guidance system may further comprise an intermediate ring corresponding to a predetermined surgically inacceptable region for the catheter.

Another aspect of the present disclosure relates to a method for implementing the guidance system of the present application.

Another aspect of the present disclosure relates to a medical device comprising the guidance system of the present application.

Another aspect of the present disclosure relates to a method and device to aid the percutaneous kidney puncture.

One aspect of the present disclosure also relates to a guidance system for dynamically guiding a surgical needle catheter or other medical device or instrument onto an organ of a patient, which is to be surgically operated, comprising:
an EM, electromagnetic, catheter, arranged for inserting into the patient and for defining a desired location to be reached by the surgical needle catheter;
an EM, electromagnetic, tracker arranged for tracking of a location and orientation of the surgical needle catheter; and
an electronic data processor arranged for:
displaying a 2D concentric-ring target;
continuously displaying a projection of a line concurrent or coincident with the surgical needle catheter onto said target, wherein said target is on a plane intersecting a tip of the EM catheter and being perpendicular to the orientation of the surgical needle catheter;
continuously displaying a plurality of concentric rings centred around the tip of the EM catheter.

In an embodiment, said concentric rings comprise an inner ring corresponding to a predetermined surgically acceptable region for the surgical needle catheter.

In an embodiment, said inner ring is centered around the tip of the EM catheter and has a radius of less than or equal to 1 mm, of less than or equal to 2 mm, of less than or equal to 3 mm, of less than or equal to 5 mm, of less than or equal to 8 mm, or of less than or equal to 10 mm.

In an embodiment, said concentric rings comprise an intermediate ring corresponding to a predetermined surgically inacceptable region for the surgical needle catheter.

In an embodiment, said intermediate ring is centered around the tip of the EM catheter and has a radius of less than or equal to 25 mm, of less than or equal to 30 mm, of less than or equal to 35 mm, of less than or equal to 40 mm, of less than or equal to 45 mm, or of less than or equal to 50 mm.

In an embodiment, said concentric rings comprise a further ring having a variable diameter depending on a spatial difference between surgical needle catheter tip and the target.

In an embodiment, said further ring has a visual characteristic which is changed when the surgical needle catheter tip deviates from the target, in particular the visual characteristic being changed when the surgical needle catheter tip goes beyond the target.

In an embodiment, said visual characteristic is a colour of the further ring, a thickness of the further ring, a fill-in of the further ring, or combinations thereof.

An embodiment comprises a 3D sound interface arranged for providing spatialized sounds according to a spatial difference between surgical needle catheter tip and the target.

An embodiment comprises a vibration interface arranged for providing spatialized vibration feedback using vibration motors, according to the spatial difference between surgical needle catheter tip and target.

In an embodiment, the plurality of concentric rings are displayed around the target on the plane intersecting a tip of the EM catheter and being perpendicular to the orientation of the surgical needle catheter.

An embodiment comprises the surgical needle catheter arranged for surgical operation of the organ.

In an embodiment, said organ is the kidney and the dynamically guiding of the surgical needle catheter is for percutaneous renal access.

It is also described a medical device comprising the guidance system of any of the disclosed embodiments.

It is also disclosed a method for implementing a guidance system for dynamically guiding a surgical needle catheter onto an organ of a patient, which is to be surgically operated, said system comprising an EM, electromagnetic, catheter, arranged for inserting into the patient for defining a desired location to be reached by the surgical needle catheter; an EM, electromagnetic, tracker arranged for tracking of a location and orientation of the surgical needle catheter; and an electronic data processor;
said method comprising carrying out by said data processor the steps of:
displaying a 2D concentric-ring target;
continuously displaying a projection of a line concurrent or coincident with the surgical needle catheter onto said target, wherein said target is on a plane intersecting the tip of the EM catheter and perpendicular with the surgical needle catheter orientation;
continuously displaying a plurality of concentric rings centred around the tip of the EM catheter.

It is also disclosed non-transitory storage media including program instructions for implementing a guidance system for dynamically guiding a surgical needle catheter onto an organ to be surgically operated of a patient, the program instructions including instructions executable by a data processor to carry out any of the disclosed methods.

One of the main functions of the surgical needle catheter is to be inserted into the body, in particular a body cavity, for surgical purposes. Additionally, a surgical needle can be used to create a percutaneous path towards the target anatomical structure to be manipulated during surgery. Alternatively, another device having a tracker EM sensor and having the function of being inserted into the body for surgical purposes can also be used.

The guidance system, method and device of the present disclosure is able to easily and safely guide the percutaneous renal access (PRA), guaranteeing that anatomical structure, in particular an organ, is not accidentally perforated and responding to current surgeon's demands. The system, method and device also improves and/or optimizes the puncture planning increasing the certainty of reaching a specific target inside the kidney.

One of the exemplary aspects of the present disclosure is to provide a new system and method to aid percutaneous kidney puncture. The guidance system of one aspect of the present disclosure is able to easily and safely guide PRA (percutaneous renal access), guaranteeing that any organ is not accidentally perforated and responding to current surgeon's demands. The disclosure is also able to optimize the puncture planning increasing the certainty of reaching a specific target inside the kidney.

The easily and safely guiding the of percutaneous renal access can be further specified in a set of specific phases:

Phase 1: Motion tracking of the surgical tools—real-time motion tracking sensors (electromagnetic motion tracking (EMT) technology to monitor the position and orientation of the needle and catheter during PRA. This phase creates a virtual environment where the information retrieved by motion tracking sensors is used to guide the surgeon during whole puncture stage.

Phase 2: User guide interface—discloses different ways to provide user feedback about the spatial relationship between the surgical tools. The outcome is a simple and intuitive user interface, at least capable of guiding the surgeon throughout the entire renal access stage, namely puncture planning and needle insertion.

Since the need of PRA has increased in recent years, the improvement in patient care and simplification of this surgical step, through the proposed phases, may lead to several exemplary non-limiting advantages:

Broaden the PRA procedure to surgeons less specialized and familiarized with MISs (Minimal Invasive Surgeries) due to an intuitive and efficient platform. Today, due to its high learning curve, only 10% of specialized urologist perform this procedure;

Eliminate X-ray imaging during PRA, which significantly decreases patient radiation exposure, especially for the surgeon who performs this intervention more than once a day;

Improve preoperative planning through the availability of accurate and complete tracking of the surgical tools;

Reduce surgery time, because one of the most time-consuming steps may be shortened through an easier puncture;

Minimize potential surgical complications caused by human errors, image misinterpretation and hand/eye coordination limitations;

Decrease errors related to target movements and tissue deformations, by permanently monitoring them during PRA;

Reduce surgery costs.

An overview of the particular ways in which the state of the art regarding PRA is improved by the present disclosure, can be made according to the following points:

A critical review that addresses the methodologies and techniques for conducting kidney targeting and the puncture step during PCNL (percutaneous nephrolithotomy);

A new real-time navigation system, based in EMT, to plan and guide PRA. It shows virtual surgical tools (needle and catheter) in 3D or 2D, according to the 3D spatial information provided by EMT sensors coupled in their tips. This framework aids the surgeon to navigate a tracked needle towards a catheter placed near the anatomical target;

3D sound interface capable of providing spatialized sounds from different point sources surrounding the user. These sounds are defined and positioned in a 3D space according to the current orientation error, that is calculated as the spatial difference between the needle tip and the puncture trajectory that the surgeon must follow; and/or Vibration device capable of providing spatialized vibration feedback using different vibration motors. These motors positioned and coupled to an elastic headband according to the eight cardinal points. Each motor generates a vibration pattern that depends on the spatial difference between the needle tip and the puncture trajectory that the surgeon must preferably follow.

BRIEF DESCRIPTION OF THE DRAWINGS

The following figures provide exemplary embodiments for illustrating the disclosure and should not be seen as limiting the scope of invention.

FIG. 12: Comparison between guidance strategies. The arrow points to the best method when comparing the average times for planning and puncturing. The asterisk gives the statistical significances (two-way ANOVA): without asterisk $p>0.05$; *$p\leq0.05$; $p\leq0.01$; *$p\leq0.001$; ****$p\leq0.0001$.

DETAILED DESCRIPTION

Figure 1:
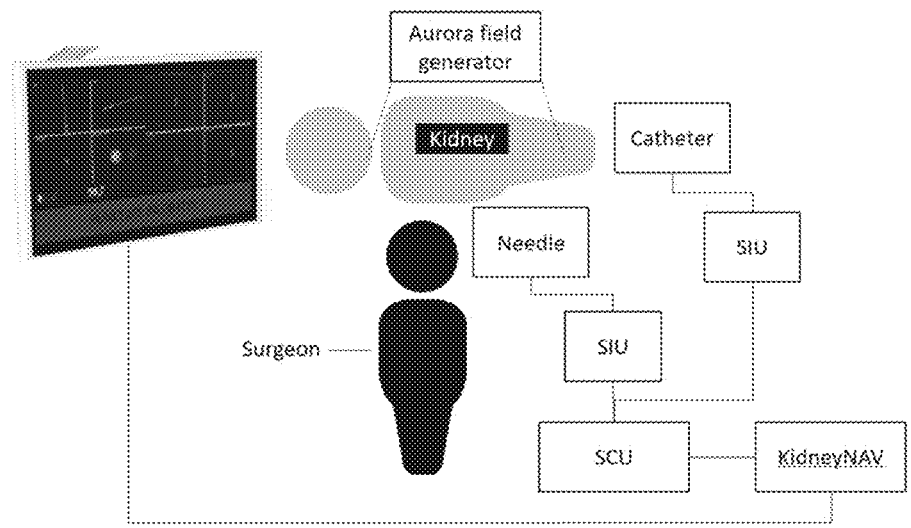
FIG. 1: Schematic representation of the surgical setup according to an embodiment when using the Aurora system [2]. The Aurora field generator creates an electromagnetic working space where the needle and catheter can be manipulated. Both tools are wired connected through the System Control Unit, SCU, to the herein described KidneyNav software according to the disclosure.

One exemplary aspect of the present disclosure relates to a guidance system, a method and a device for dynamically guiding a surgical needle catheter or other medical instrument onto an organ of a patient. In particular, the present disclosure relates to a guidance system, method and device to aid in the percutaneous kidney puncture.

The following pertains to motion tracking for surgical navigation, in particular electromagnetic tracking for puncture guidance, further in particular the Aurora system (NDI, Waterloo, Canada). EMT potentially can be used to guide PRA interventional procedures, since it can provide accurate tracking without the line-of sight requirements. In order to track medical devices such as needles and catheters this system comprises the following hardware devices: field generator, sensor interface units (SIU), system control unit (SCU) and electromagnetic sensors. The Aurora™ system is but one example of an EMT system, used according to the present disclosure. Although it is to be appreciated similar systems will work equally well with the disclosed technology.

In accordance with one exemplary embodiment, the SCU includes one or more processors, a graphics processing unit (GPU), memory, an audio interface for the headphones discussed hereinafter, an audio card or equivalent audio processing system and a controller for actuating any tactile feedback.

The SCU can interface with the SIUs using any known communication protocol and/or interface(s) including wired or wireless interfaces. The SCU and KidneyNAV can also be connected to one or more display unites and configured to display the visual guidance as discussed herein. Communication between the SCU, KidneyNAV and the surgeon's feedback mechanisms can be wired or wireless, such as using Bluetooth®, to send signals to the headphones and/or tactile feedback device(s) such as the vibrotactile headband. It is to further be appreciated that the SCU and KidneyNAV could be combined with virtual reality or augmented reality goggles such that the information displayed on the display could be presented in these goggles in 2D or 3D.

The planar field generator emits a low-intensity and varying electromagnetic field that establishes a working volume. When the electromagnetic sensors are placed inside this working volume, small currents are induced in the sensors. These induced voltages are measured by the SCU that calculates the sensors position and orientation. The SCU also transmits the positional data to a host computer using a serial port connector or other communication port/protocol, for subsequent processing and navigation.

The electromagnetic sensors are connected via a SIU to the SCU. This SIU works as an analog-to-digital converter and amplifier of the electrical signals from the sensors to an SCU, decreasing the possibility of electromagnetic interferences in the operating room.

The low electromagnetic field strength can safely pass through human tissue, making it an ideal system to track surgical instruments inserted inside the human body through natural orifices or small incisions.

Finally, the electromagnetic sensors can be embedded into the working surgical tools or devices. For this embodiment, one may preferably acquire two modified surgical instruments: one 18 G/180 mm Chiba needle; and one ureteral catheter with 1.1 mm diameter and 2 m length. Both incorporate an electromagnetic sensor with 5 DOF at its tip, not being able to infer the orientation about their long axis (roll axis).

The following pertains to methods. In particular, the following pertains to EMT Navigation. The introduction of EMT navigation, for example the Aurora system, in the PRA workflow will modify the first two PCNL surgical stages: (a) the trans-urethral catheter placement and (b) the percutaneous puncture.

The following pertains to trans-urethral catheter placement. On the first surgical step, an Uretero-Reno-Fiberscope Flex-X™ from Karl Storz or comparable device is transurethrally placed from the urethra towards the desired renal calyx.

In contrast to the currently used technology, the catheter is guided towards the anatomic target using the Flex-X™ camera without requiring other medical imaging modalities. Furthermore, since Flex-X has a working channel of 1.2 mm, it allows the integration of a positioning and orientation electromagnetic sensor with six DOFs (Degrees of Freedom) at its tip from Aurora motion tracking system (NDI, Waterloo, Canada). Here the electromagnetic sensor, located at the Flex-X™ tip, acts as an anatomic target locator, operating as a GPS (global position system) for the puncture site.

According to Flex-X™ tip orientation it is possible to place the sensor in the desired calyx, where the calculi target is located, allowing the surgeon to choose the best virtual trajectory for the percutaneous puncture.

The following pertains to puncture stage. On the second surgical step, a virtual trajectory will be determined by the relative orientation and position differences retrieved in real-time by both needle and catheter EMT sensors.

This virtual trajectory display will be used to confirm that the catheter and needle are parallel aligned. If necessary, the surgeon can redefine the catheter orientation, and the virtual trajectory will be real-time updated. This procedure provides constant real-time positioning feedback (beep sound and/or 3D representation) to the surgeon, allowing the surgeon to accomplish a perfect orientation of the needle at all times, even in the presence of anatomical changes, such as tract dilatation, respiratory movements and needle deflections, among others.

The beep sound was generated by asynchronously and repetitively playing a MP3 or comparable sound file with 0.15 seconds of duration. This sound was played with a frequency calculated with the common linear equation: $y=mx+b$. The slope m of such equation was given by the distance between the catheter and needle EMT sensors. The embodiment includes that the frequency should increase when the needle tip is close to the catheter tip. The x and b were experimentally calculated (x=17 and b=60), by moving one sensor towards and away from another and by qualitatively evaluate the sound feedback, although other values are possible.

Concerning this new tracking disclosure, FIG. 1 shows a new surgical setup. Now it is possible to track accurately the needle tip with an electromagnetic sensor (5) and the anatomical target using a tracked catheter (6). In contrast with the Polaris system, the Aurora tool should be wired connected to the SCU (4 and 7) that communicates with the KidneyNav software (1 and 2).

The following pertains to Animal Preparation. This EMT approach was tested using different female pigs (Sus scrofus domesticus) with various weights (25-35 Kg). Before surgery, the animals were fed with liquids for 3 days and then restrained from food (24 hours) and water (6 hours) before the surgical tests.

All procedures were carried out with the pigs under general anesthesia, with 5.0 mm endotracheal intubation and mechanical ventilation. Pre-anesthesia medication consisted of an intramuscular injection of 32 mg/mL azaperone, reconstituted with 1 mg/mL midazolam with a dose range of 0.15-0.20 mL/kg.

The venous access was obtained through an intravenous line placed at the marginal ear vein. The anesthesia was induced with 3 μg/kg fentanyl, 10 mg/kg thiopental sodium, and 1 mg/kg vecuronium. It was maintained with 1.5% to 2.0% of sevoflurane and a perfusion of 1 mg/kg per hour of vecuronium. All pigs received an intramuscular injection of 1 g ceftriaxone before the tests beginning.

The following pertains to Experiments. In vitro and in vivo experiments were performed to evaluate the accuracy and performance of the EMT framework for PRA. Ex vivo tests aimed to understand and quantify the Aurora system technical characteristics, such as precision, accuracy and critical system problems e.g., electromagnetic interferences. On the other hand, in vivo animal trials, with more dynamic characteristics, aimed to define and evaluate the surgical setup, planning and puncture time, system reliability and efficiency for PRA.

The following pertains to laboratory trials, in particular electromagnetic interferences. The purpose of a test was to investigate error sources that might compromise the EMT accuracy during surgical navigation.

This test starts by putting the field generator on a position arm which offers flexible setup options around an object of interest, e.g. abdominal phantom placed in an electromagnetic free environment. Then, both the needle and catheter sensors, adjacently fixed to each other, were moved randomly along the working volume. The positional difference between both sensors was transmitted and stored to a host computer. In absence of electromagnetic interference, the difference between both sensors should be a constant with negligible variances.

Because one aims to quantify the mean accuracy within this navigation volume, different surgical tools made with different material were placed inside the navigation volume and in the vicinity of the electromagnetic sensors. For each material, one compared the sensors positional difference with the values acquired when any electromagnetic interference exists. The following materials were evaluated due to their usage during PCNL:

Stainless steel: the majority of medical instruments are manufactured with stainless steel due to its strength and durability. One evaluates electromagnetic interferences of this material by using different surgical instruments such as ureterorenoscope, cytoscope, telescopes, scalpel and forceps.

Tungsten Carbide: is used in the manufacture of such instruments as needle holders, scissors, pin cutters and pliers;

Mild steel: this metal is almost obsolete because its tendency to chip and contaminate other instruments. Only scissors were used to test this material.

Aluminium: only certain instrument parts and cases are manufactured from aluminum due to its lightweight, e.g. handle and or body of the instrument and not the tool itself (scissors and forceps)

Titanium: The high cost of using titanium for instrument manufacture is often prohibitive. Due to its lightweight, it is commonly used for microsurgery tools, e.g. forceps, laparoscopic tools.

The following pertains to Animal Trials. The animal experimental studies were approved by the ethical review boards of Minho University, Braga (Portugal). The animal was monitored by a veterinary anesthesiologists throughout the study.

Figure 2:
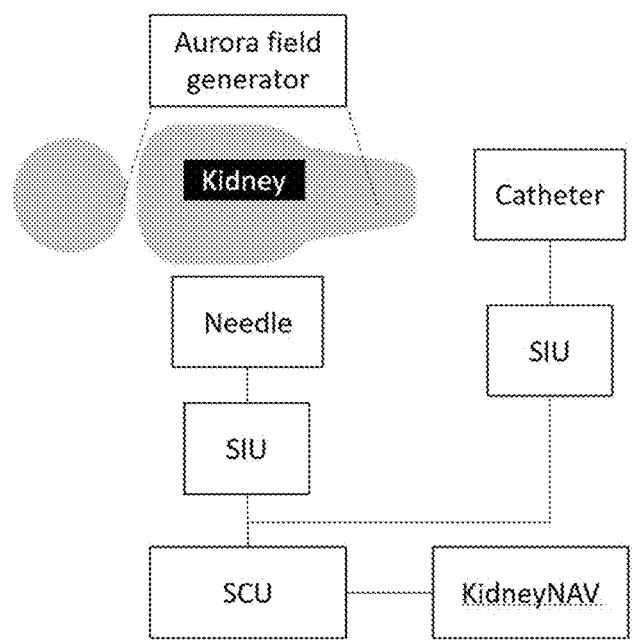
FIG. 2: Overview of the animal trial for percutaneous collecting system access.

This experiment starts by placing the pig in supine position. This first stage is used to identify the ureteral orifices of both kidneys using a rigid cystoscope. Then, ureterorenoscopies were performed bilaterally. An ureterorenoscope with 1.2 mm working channel allowed to put the ureteral catheter into the desired puncture site. FIG. 2 represents the experiment setup.

After positioning the ureterorenoscope at the puncture site, resorting to a direct video view, the surgeon inserted the needle into the calyceal fornix by the following actions:
1. Orientate the needle through a virtual direct path, aligning the needle tip with the target position;
2. Puncture the first skin layer and repeat step 1);
3. Drive the needle through the selected path, until it reaches the anatomic target (confirmed by the ureterorenoscope video camera).

The percutaneous punctures were performed for each pig at the ureter half-way between the kidney and the urinary bladder and in renal calyces in order to evaluate the puncture location influence.

The following pertains to Outcome Measurements. The following surgical parameters were evaluated in order to ascertain if the proposed tracking solution confers any advantage to the surgeon performing PCNL:
a. Planning time: time needed by the surgeon to evaluate the virtual trajectory displayed at the software and orient the needle at skin surface;
b. Number of attempts: number of tries to reach the puncture site;
c. Puncture time: time needed to perform a successful renal puncture from the skin surface to the puncture target. When the needle tip was visible by the ureteroscope camera, the needle pass was considered complete.

The experiments were performed by an expert surgeon and a resident in order to avoid a supposed bias related to surgeon ability. Furthermore, the puncture location was also analyzed as a variable influencing the above outcomes.

The following pertains to Results, in particular of Laboratory Trials, in particular of Electromagnetic Interferences. The needle and catheter were adjacently placed with 10 millimeters distance between them. No relevant interferences were found when using stainless steel, titanium or tungsten carbide. In these cases, the maximum error was not significant (<0.2 mm). The catheter can be placed inside the ureterenoscope or cytoscope working channel without losing tracking accuracy.

When using mild steel or aluminum instruments one found that the error increase proportionally with the distance between the sensors and the ferromagnetic material. Maximum errors of 8 and 15 mm were found when maneuvering EMT sensors in the working volume periphery and a mild metal or aluminum, respectively, were placed in the middle of the working volume. When aluminum tools, e.g. forceps or scissors were manipulated ~7 cm away from the electromagnetic sensors, the maximum error was less than 1 mm.

The following pertains to Animal Trial. Overall 24 punctures were successfully performed without any complications: 12 in middle ureter and 12 in the kidney calyx (lower, middle or upper kidney calix).

Table 1 summarizes measured outcomes for whole procedures. Planning time was longer for the ureter case than the kidney (median 15 versus 13 seconds, range 14-18 versus 11-16; p=0.1).

Likewise, time to achieve ureteral puncture was significantly longer than kidney puncture, requiring 51 (range 45-67) and 19 (range 14-45) seconds (p<0.01), respectively. Two attempts were needed to carry out the ureteral puncture, contrasting with a single attempt for the kidney (p<0.05). When comparing the puncture time, planning time, number of attempts and final distance (Table 2), regarding the percutaneous renal access for the upper, middle and lower calyx, one achieved non-significant differences (p>0.05).

TABLE 1

Surgical outcomes according to puncture location.

| Measures | Puncture Site | | |
|---|---|---|---|
| Median (min − max) | Kidney calyx | Ureter | P* |
| Planning Time (s) | 13 | 15 | 0.1 |
| | (11 − 16) | (14 − 18) | |
| Puncture Time (s) | 19 | 51 | 0.003 |
| | (14 − 48) | (45 − 67) | |
| Number of Attempts | 1 | 2 | 0.01 |
| | (1 − 2) | (2 − 4) | |
| Final Distance | 2.1 | 1.9 | 0.79 |
| | (1.5 − 2.7) | (1.4 − 2.7) | |

*Mann-Whitney test between kidney calyx and ureter

TABLE 2

Surgical outcomes according to the kidney calyx.

| Measures | Kidney Calyx | | | |
|---|---|---|---|---|
| Median (min − max) | Upper | Middle | Lower | P* |
| Planning Time (s) | 15 | 14 | 13 | 0.51 |
| | (12 − 17) | (12 − 16) | (10 − 15) | |
| Puncture Time (s) | 25 | 19 | 20 | 0.9 |
| | (14 − 48) | (14 − 48) | (14 − 40) | |
| Number of Attempts | 1 | 1 | 1 | 0.62 |
| | (1 − 2) | (1 − 2) | (1 − 2) | |
| Final Distance | 2.0 | 2.1 | 2.1 | 0.79 |
| | (1.8 − 2.2) | (1.5 − 2.5) | (1.9 − 2.7) | |

*Mann-Whitney test

When results from experts and residents are analyzed independently (Table 3), one verifies that, despite non-significant statistical differences (p>0.05), there was a slight tendency of higher puncture and planning times, as well as, a great number of attempts for residents.

TABLE 3

Surgical outcomes according to the kidney calyx and ureter punctures.

| Measures Median (min − max) | Kidney Calyx | | | Ureter | | |
|---|---|---|---|---|---|---|
| | Resident | Expert | p* | Resident | Expert | P* |
| Planning Time (s) | 15 | 13 | 0.06 | 17 | 15 | 0.08 |
| | (13 − 17) | (10 − 16) | | (17 − 19) | (15 − 16) | |
| Puncture Time (s) | 29 | 19 | 0.38 | 66 | 48 | 0.06 |
| | (14 − 48) | (14 − 34) | | (64 − 68) | (46 − 50) | |
| Number of Attempts | 1 | 1 | 0.98 | 4 | 2 | 0.99 |
| | (1 − 2) | (1 − 2) | | (3 − 4) | (2 − 3) | |
| Final Distance | 2.1 | 2.0 | 0.72 | 1.8 | 1.6 | 0.12 |
| | (1.5 − 2.2) | (1.8 − 2.7) | | (1.6 − 1.9) | (1.4 − 2.0) | |

*Mann-Whitney Test

Computer navigation systems, based in EMT technologies, are an attractive research area and have been suggested for different surgical procedures [9]. From the PRA point of view, it was performed several in vitro, ex vivo and in vivo experiments to evaluate the efficiency of the KidneyNav framework, working together with EMT Aurora system.

The following pertains to the Aurora System. The great advantage of Aurora over optical systems, such Polaris, was the ability to track small EMT sensors inside the human body without any line-of-sight requirements [1].

The disclosure preferably demands endoscopic imaging for real-time monitoring of the puncture target and two EMT sensors. The ureteral catheter and needle, both integrating an Aurora EMT sensor at its tip, are able to retrieve in real-time the position and orientation. The catheter remained associated to the puncture target (worked as a 3D real-time locator) and was permanently monitored by the EMT sensor and the ureterorenoscope video camera. Therefore, it followed in real-time all the anatomic tissues deformations and movements—originated by the respiratory cycle and also by those induced to the patient. The surgeon inserted the needle guided by the virtual puncture path displayed in the KidneyNav interface.

An important proof-of-concept step was also achieved by succeeding in performing a direct ureteral puncture, even though the procedure took significantly more time, due to the ureteral movements, ureter small diameter and soft consistence, which made the needle glide on its surface. Even though these preliminary results provide prospective paths for other applications (e.g. Percutaneous Ureteral Lithotripsy), the main objective was to further corroborate the efficiency of the purposed puncture method in a small target cavity.

Interesting of note, no difference in operator skill was found in performing the puncture. Whereby, it is reasonable to speculate that this tracking solution may reduce the number of cases needed to perform an appropriate collecting system access and make it easier. Specific literature reports that the learning curve completion for PCNL surgical competence around 60 cases. Considering the kidney access one of the most challenges phases, in this study a resident achieved the same skill level of an expert surgeon with only twelve cases.

The safety efficacy of different surgical positions for accessing the collecting system has been a controversial issue, with currently no established best practice consensus. The use of a real-time 3D trajectory proposed in this work may broaden the use of supine position for the whole PCNL procedure. In this case, the surgeon does not need to reposition the patient (decreasing surgery time in about 30-40 minutes) and may improve levels of comfort for both patient and surgeon as described in the literature. On the other hand, when the patient is repositioned, there is a reduced risk of access dislodging, since the catheter remains permanently monitored by the EMT sensor and the ureterorenoscope camera.

Medical imaging assistance to puncture commonly requires approximately 10 minutes, often guided by X-Ray based imaging and in vitro conditions. Comparing the related results, one has achieved a puncture time improvements between 75 and 85% without any X-Ray need.

Due to its advantages, the Aurora system has been extensively tested in recent years in different clinical and non-clinical environments [1]. Different works have reported errors of 0.71±0.43, with a maximum 3D root mean square positional accuracy of 2.96 mm. Although these values are higher than the Polaris accuracy, it remains highly suitable for PRA purposes [11].

Although Yaniv et al. [1] reported that electromagnetic systems may be susceptible to environment interference in the operating room, the techniques disclosed herein did not experience any kind of interference that could tamper the tracking information. By evaluating the impact of the surgical instruments, composed by different metals (aluminum, stainless steel, titanium, tungsten carbide and mild steel), one creates a more comprehensive list of requirements when using an EMT system in the operating room. Results show that only mild steel or aluminum can influence the error-proneness of EMT sensors. However, this may not represent a problem since mild steel or aluminum instruments have been replaced by stainless steel ones [1]. But, in order to guarantee that the system accuracy is not degraded, aluminum or mild metal should possibly not be used during the surgical procedure. At least, they should not be placed inside the working volume while the puncture is being performed.

Other important evaluation data was the intrusiveness of such modality. In contrast to other navigation frameworks, it will not increase the procedural time because the proposed system does not have a large setup and does not require additional steps like immobilization of the patient, preparation of the hardware, registration setup, or initializing of navigation components [1].

The motion tracking field generator should be placed on the surgical stretcher as near as possible to the kidney abdominal area (or other area being operated upon) and with an appropriately orientation to minimize the probability of interference distortions. All other possible electromagnetic disturbance sources, such as, cellphones and usual operating room equipment should kept at least 1.5 meters away from the working volume. The KidneyNav interface will advise when some possible interference exists or if the instruments are being maneuvered at the limits of the working volume.

When compared to the Polaris, the Aurora system can use wires to transmit the information between the EMT sensors and control unit and a field generator positioned close to the interventional area. However, these did not restrict the access to the abdominal area, not being a limiting factor in any of the experiments. Since sensors are placed inside the human body during all operation, there was no need for a registration and calibration procedure.

Hereupon, the proposed solution may be the simple and easy way to select and follow the correct puncture path, as well as acquire the required skill to perform PCNL regardless of calculus site, large or multiple renal calculi, or an ectopic or malformed kidney.

The following pertains to multi-sensorial guidance interface. Visual interfaces have been proposed over the years for biomedical applications covering the diagnostic, planning and guidance of several surgical procedures. Currently available visual interfaces, aid surgeons throughout the entire surgical procedure, reducing the risks and possible unknowns [12].

Although new algorithms and registration techniques have been explored to link virtual and real worlds, the interpretation of 2D images or 3D reconstructions are still a challenging task. For intraoperative complex procedures, visual interfaces may only provide good guidance capabilities for specific points of view. Often, surgeon's skills and expertise strongly affect the surgical outcome.

In addition to the information received through our sight, audio and tactile information are nowadays becoming commonplace ways of transmitting information. Hearing and touch are the second and third major human senses, respectively, being two promising and unique alternatives or complementary modalities for visual systems. Consequently, it allows the development of innovative hand- and eyes-free interfaces.

The aspect of using new ways of feedback for puncture guidance during PRA, concerns the ability to create accurate and precise localization of the needle tip with respect to the anatomical target.

The following pertains to audio feedback systems. First audio feedback methodologies have been explored due to their ability to create, process and localize sounds from complex data in a 3D space. Since computational requirements to generate audio are much smaller than for 3D graphics, these auditory interfaces were created in order to overcome technological limitations, such as limited real-time refresh rates, image poor resolution and rendering capabilities.

Nowadays, audio feedback is an attractive area of exploration for a wide range of medical or nonmedical applications [13]. Due to the ability of surrounding the listener with sounds at specific locations, sound applications have emerged to create an immersive environments for computer games [13], warning systems for civil aircraft [13], flight and military simulations, guidance interfaces to blind people, night vision systems, airplane cockpit, guidance to athletes, augmented reality systems, perceptual representation of biomedical data and heart rate monitors [12].

To the best of our knowledge, audio feedback for computer aided surgery have only been only explored by four groups [12]. Preliminary works were reported by Weber et al. [12], describing an audio system to guide a biopsy needle when perforating a gelatin phantom. Although they describe an application with great potential, quantitative or qualitative results are not reported.

Another audio feedback system, presented by Cho et al., guides the surgeon to a cochleostomy location. The authors generate warning tones when an optical tracked drill is closer to the target (tones of 300 Hz) or reaching the target (tones of 900 Hz).

From the analyzed literature, audio feedback advantages include faster processing data, high temporal resolution, parallel data streams and improves the degree of focus on the task at hand. Moreover, it creates an effective way to overcome the visual overload from complex data and due to its omnidirectionality, i.e., allows perceptions from any point in space without occlusions.

Low spatial resolution and perception, sound interferences, dependence of user are the main shortcomings [12] of the above techniques.

The following pertains to vibration feedback systems. Similar to audio feedback systems, the usage of vibrotactile feedback has also been described in literature. For instance, vibrotactile has been reported as useful in improving awareness of critical events such driver responses, spatial guidance in pedestrian navigation, alert systems for blind or visually impaired persons, gesture guidance, human-computer interaction improving realism with tactile display interfaces, immersive sensations in computer games, body posture improvements (Janssen et al., 2010), and assistance in rehabilitation.

Hence, various innovative and disruptive devices were proposed for being attached for different human parts, e.g., head [14], fingers, forearm, hand, upper body, tongue and foot.

The head has been the most preferable site for vibration wearables (e.g., headbands [14], headphones and glasses). They have been studied in various environments, because they do not restrict the users maneuverability (e.g., devices used in fingers, forearm, and hand), verbal communication (e.g., devices used in the tongue) or touch sensation (e.g., gloves).

Even being an preferred place for receiving feedback, some authors warned that the head sensitivity is not the same throughout whole area. Myles et al. and Weber et al. study and evaluate the sensibility of head surface. Both studies stated that vibration sensitivity is different for different head locations, where the crown of the scalp was reported as the least sensitive to vibration stimuli relative to areas close to the temples, forehead, and back of the head (most sensitive area).

Even ergonomics, positional efficiency and accuracy of a vibrotactile headband has already been studied [14], pattern codification for guidance, the preferred number of actuators and testing in real situations are still needed.

The following pertains to audio and vibration feedback for PRA. From the reported applications, it is clearly seen that audio or vibrotactile feedback can considerably highlight 3D orientation and guidance, decreasing the dependence of visual faculties and improving insight into virtual data. They often improve perception capabilities, which may be altered due to continued procedures, fatigue, inaccurate insight and decrease of attention.

When compared to other medical technologies routinely used for guidance (e.g. motion tracking systems, robotic devices, improved surgical tools, imaging systems), audio or vibrotactile feedback are relatively unexplored. The wider acceptance of such modalities will mostly depend on the quality and quantity of transmitted information, but also if the user can effectively learn how to use it.

In addition to the 3D feedback provided from the KidneyNav interface, this work explores the potentiality of new guidance interfaces including an improved 2D visual interface (from now on referred as NeedleView), a vibrotactile headband and 7.1 headphones able of generating 3D directional sounds.

The following pertains to methods, in particular to an overview. In this section, we propose the application of a multisensorial feedback platform combined with the previous described 3D view of the KidneyNav to develop a more intuitive guidance system. Upon each occurrence of the needle tip deviating from the path to reach the target, a set of audio and/or vibration signals will be generated and transmitted to the surgeon.

Figure 3:
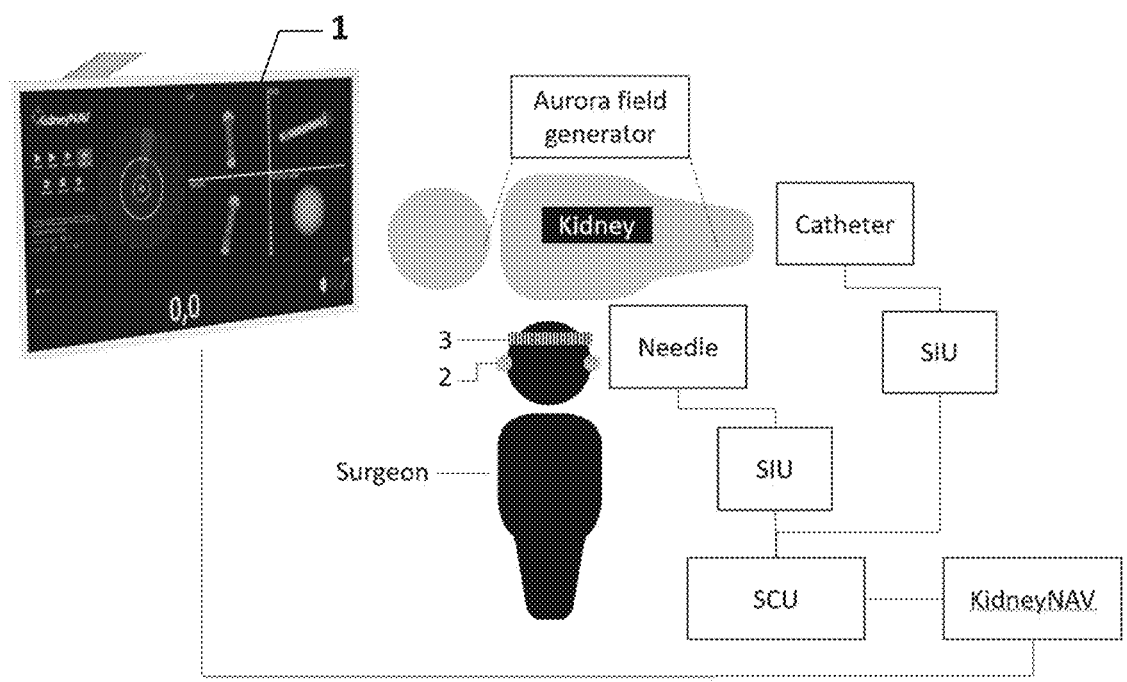
FIG. 3: Representation of the new surgical setup considering the multi-sensorial interface: 1) NeedleView, 2) 7.1 headphones and 3) vibrotactile headband.

Such information will be perceived from a vibrotactile headband, 7.1 headphones and the NeedleView, that will aware and guide the surgeon towards a preferred path (FIG. 3).

Figure 4:
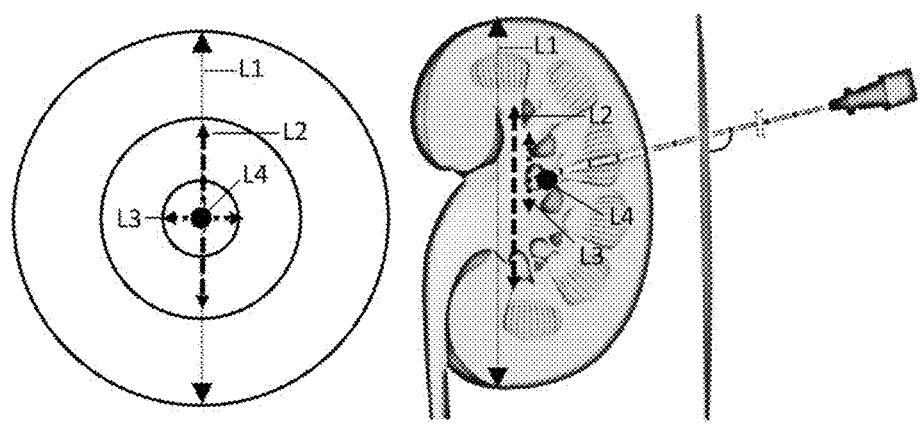
FIG. 4: Representation of the NeedleView interface (right). The vertical arrows (white, green, yellow and red) show the size correspondence between the circles diameter and the kidney anatomy.

The following pertains to NeedleView. Sight devices used to support instruments aligning (e.g. weapons, airplanes, telescopes, etc.) were prior art to the disclosure of the NeedleView. FIG. 4 shows the developed target sight. Vertical and horizontal alignment for the perfect needle orientation is achieved when a blue sphere is placed inside a white disk (although other color schemes are possible).

Figure 5:
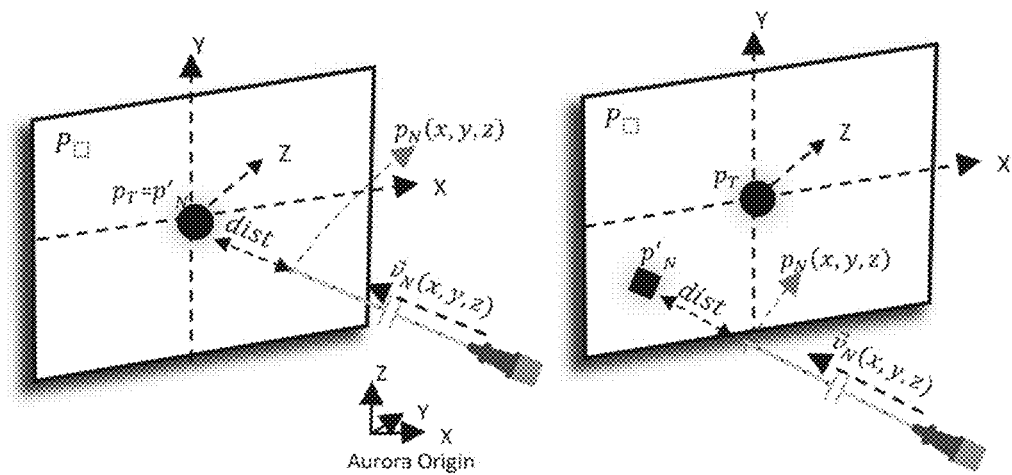
FIG. 5: Representation of the ray-plane projection method to create the NeedleView visual interface.

Once the needle is aligned in the right position, a green label showing the distance to the target will be displayed to the user. If any deviation occurs, a red label will be shown. Likewise any sight, the needle tip will reach accurately the anatomical target if the needle is inserted along the path without any deviation. Different color disks (white, green, yellow and red in FIG. 4) may be used to implement a score system that gives information about the current error with respect to the target:

White region informs the user that the needle will reach the target within a 2 mm error (approximately the size of a minor kidney calyx);

Green region informs the user that the needle will reach the target with a maximum error of 10 mm (proximately the side of a kidney medulla);

Yellow region informs the user that the needle will reach the target with a maximum error of 25 mm (proximately the side of a kidney pelvis);

Yellow region informs the user that the needle will reach the target with a maximum error of 50 mm (proximately the side of a kidney size);

The blue sphere is drawn according to a method that projects a ray in a 3D plane (FIG. 5). Let $p_N(x, y, z)$ be the current needle position and $\vec{v}_N(x, y, z)$ a 3D vector defined at $p_N(x, y, z)$ and the orientation of the needle tip. Let P be a plane defined by the target position $p_T(x, y, z)$ and a normal $\vec{v}_T(x, y, z)$. The needle will accurately reach the target ($p_T(x, y, z)$) if a ray $\vec{R}_N$ starting at its tip position at $p_N(x, y, z)$ follows a direction $\vec{v}_N(x, y, z)$.

The NeedleView represents graphically the intersection of the ray $\vec{R}_N$ with P at a projection point $p'_N(x, y, z)$. When $p_T(x, y, z) = p'_N(x, y, z)$ the user is following the correct trajectory.

Any point $p_{Ray}(x, y, z)$ along $\vec{R}_N$ can be calculated according to (Equation 1):

$$p_{Ray}(x,y,z) = p_N(x,y,z) + t \times \vec{v}_N(x,y,z) \quad \text{Equation 1}$$

where t is a free constant that gives different points away from $p_N(x, y, z)$. $p'_N(x, y, z)$ is calculated by solving this t parameter (Equation 2).

$$t = -\frac{\vec{p}_N(x, y, z) \cdot \vec{v}_T(x, y, z)}{\vec{v}_N(x, y, z) \cdot \vec{v}_T(x, y, z)} = \quad \text{Equation 2}$$

$$-\frac{|\vec{p}_N(x, y, z)| \times |\vec{v}_T(x, y, z)| \times \cos(\theta)}{|\vec{v}_N(x, y, z)| \times |\vec{v}_T(x, y, z)| \times \cos(\alpha)}$$

$\vec{p}_N(x, y, z)$ is a vector defined between $p_N(x, y, z)$ and $p_T(x, y, z)$; $\theta$ is the angle between $\vec{p}_N(x, y, z)$ and $\vec{v}_T(x, y, z)$; and $\alpha$ is the angle between $\vec{v}_N(x, y, z)$ and $\vec{v}_T(x, y, z)$. Finally, by solving Equation 2 in Equation 1, $p'_N(x, y, z)$ is given by Equation 3:

$$p'_N(x, y, z) = p_N(x, y, z) + \quad \text{Equation 3}$$

$$\left( -\frac{|\vec{p}_N(x, y, z)| \times |\vec{v}_T(x, y, z)| \times \cos(\theta)}{|\vec{v}_N(x, y, z)| \times |\vec{v}_T(x, y, z)| \times \cos(\alpha)} \right) \times \vec{v}_N(x, y, z)$$

Note that if $\text{dot}(\vec{v}_N(x, y, z), \vec{v}_T(x, y, z)) = 0$, the needle orientation and target plane are perpendicular. To avoid such cases, at the beginning of the puncture and after performing an initial orientation, $\vec{v}_T(x, y, z)$ is automatically set as $\vec{v}_N(x, y, z)$.

The following pertains to audio feedback. 3D audio feedback was obtained by creating positional sounds varying one or more of the following characteristics: pitch (sound frequency), loudness (sound intensity) and playing location (sound source with a particular 3D location).

The following pertains to audio channels. According to the number of source sounds it is possible to classify sound systems as mono (1 discrete audio channel), stereo (2 discrete audio channels) and surround (N audio channels).

A mono system only produce sounds from a single source, being not able to transmit surround information. Stereo systems are able to reproduce sound from two independent sound sources, placed at the left and right of the listener. By changing the gain of each channel, it is possible to notice sound in the line between the left and right channel. Common methods to produce 3D sounds based on stereo systems are based on modifications of audio amplitude or on the delaying the arrival of the sound into the listener. Lastly, true surround sound is created by placing sound sources anywhere in 3D space. The spatial sound resolution is dependent in the number of sound sources surrounding the listener.

This work makes use of 7.1 headphones for producing surrounding audio: 7 directional channels left, center, right, left surround, right surround, left rear surround and right rear surround and 1 subwoofer that enhances low frequencies. These headphones are able to produce spatialized sound in the horizontal listener plane. Still, the reproduction of elevation sounds is still limited.

The following pertains to Audio APIs. A 3D audio space can be created using an audio API. The most known are OpenAL and EAX (Environmental Audio Extensions) from Creative Technology, Ltd. and DirectSound3D produced by Microsoft. EAX works as an audio extension for OpenAL and DirectSound3D and implements different audio effects (e.g. echo, reverberation, distortion, occlusions, exclusions, obstructions). Therefore, it cannot be used, by itself, to create a 3D sound world. On the other hand, DirectSound3D and OpenAL includes common functionalities [13]:

Audio Contexts: an audio environment can be described as consisting of a listener and source sounds. One single context is created for each sound card;

Spatialized Audio: a listener is created per context and is positioned in a 3D world. Then, different audio sources are also defined and placed in the same world. The spatialization is accomplished by attaching a specific buffer to each audio source. A buffer consists in the audio data originated from loading a sound file (e.g. MPR, PCW) or by creating configurable sound functions such as sinusoids with different frequencies.

High level functions to play, restart, rewind or loop each audio source under the sound card or CPU;

Audio Attenuation functions: the audio is attenuated as function (linear or exponential) of the distance between the listener and audio source;

Static and Streaming Audio: can play data completely stored in memory and stream buffers while continually read new portion of data at specific time intervals;

Pitch and frequency manipulation;

Doppler effect: automatically modifies the audio source frequencies giving an effect of different moving velocities of an audio source.

DirectSound3D presents some additional capabilities over OpenAL, since it supports audio effects and live voice. However, it is limited to wave files data, is more difficult to implement and only works under Windows®. In contrast, OpenAL supports the most used operating systems such Windows®, Android®, Linux® and Apple®. Consequently, OpenAL was chosen as the most suitable API platform concerning the trade-off between potentialities and facility of implementation. By combining all the above characteristics in a single framework, it is possible to create a fully immersive sound environment, with audio sources placed at strategic positions, to precisely and accurately aid the needle tip orientation with respect to the target position.

The following pertains to 3D audio world. The audio feedback preferably follows the same strategy as the NeedleView. The aspect of using audio to correct needle orientation is based on creating and positioning different audio sources in a 3D space around a centered listener (FIG. 6).

Sound from different positions will reach the listener with different directions. By internally analyzing this direction, the listener will be able to ascertain the corrections to be made. The error at the horizontal plane P of the NeedleView are used to activate or deactivate the playing sources.

Figure 6:
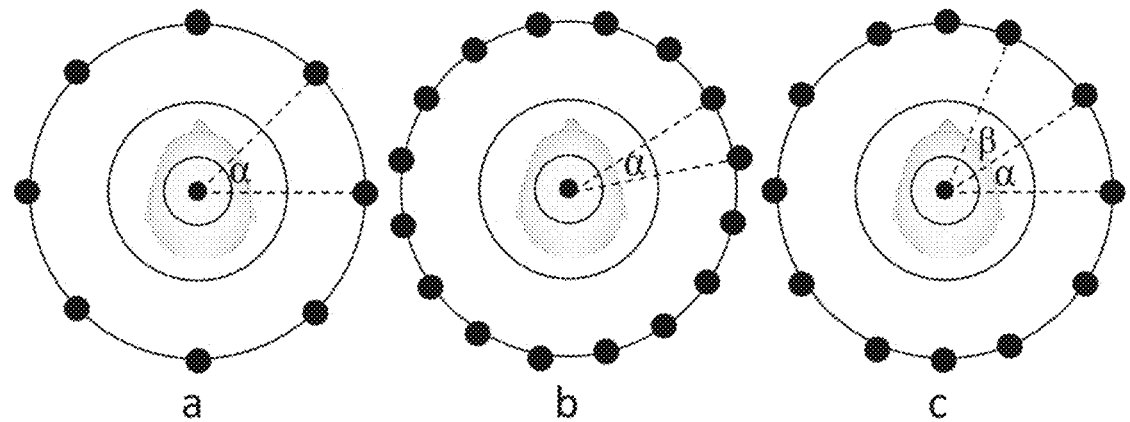
FIG. 6: Representation of 3D sound configurations around the listener via a direct path. Each sound source is represented by a red circle. a) 8 sources equally spaced by $\alpha=45$ degrees; b) 16 sources equally spaced by $\alpha=22.5$ degrees; c) 12 sources with two different angles: $\alpha=22.5$ and $\beta=56.25$ degrees.

Since the reliability of audio spatialization is dependent on the number of sources, three different configurations were tested (FIG. 6): 8, 16 and 12 source configurations (8SC, 16SC, and 12SC in FIG. 6-*a*, -*b* and -*c*, respectively).

The following pertains to positional feedback. Errors from the preferred trajectory are used to set different audio buffers and to activate/deactivate audio sources from where the sound will be emanated.

Since changes in the needle orientation are correlated with changes in the listened sound, three different strategies were implemented to accurately alert and guide the listener during needle insertion. All of sound strategies are based on the variation of the sound pitch, loudness and source location.

Figure 7:
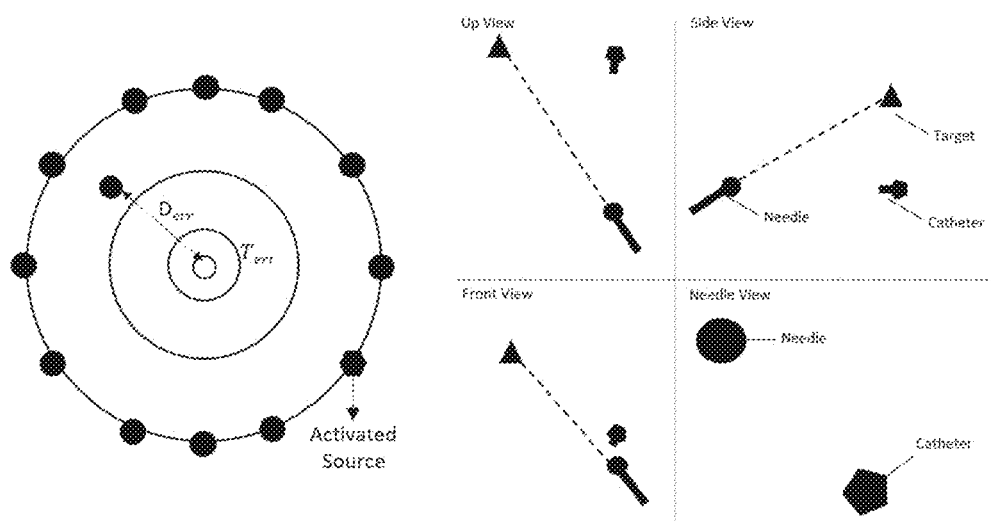
FIG. 7: Representation of the visual guidance interface while playing a sound source.

The following pertains to a first sound strategy—SS1. The audio loudness is calculated according an error function, with respect to the preferred trajectory. When the needle is following the correct path, i.e., the target can be reached with an accuracy less $T_{err}$ mm, no sound will be produced (loudness is 0). As shown in FIG. 7, for errors higher than $T_{err}$, i.e. the needle starts moving away from the correct path, the sound source with opposite direction to the error will start playing.

Figure 8:
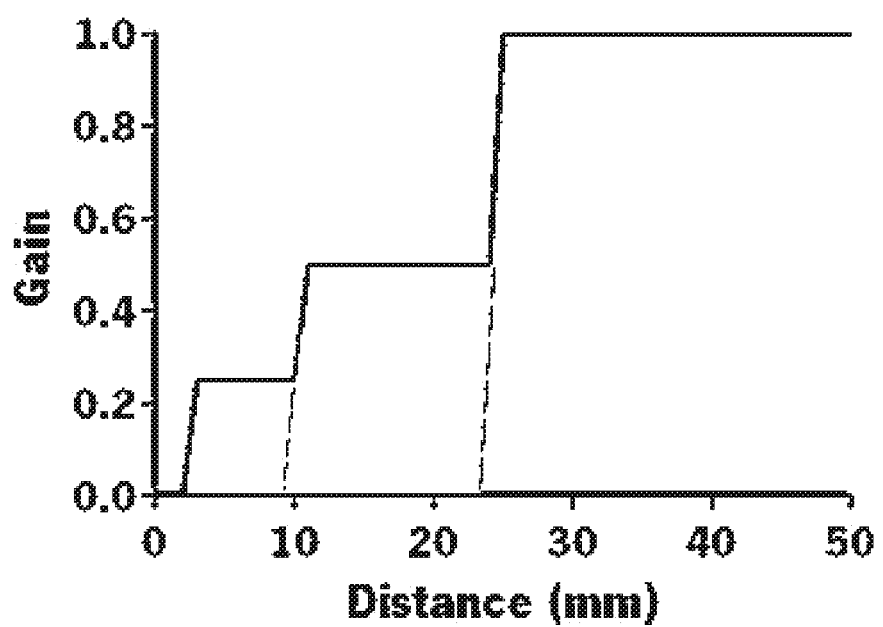
FIG. 8: Step function that gives the sound loudness gain according to the error region.

$D_{err}$ is calculated through the Euclidean distance from the vertical and horizontal errors and is used to control the source loudness gain from 0 (no sound is listened) to 1 (maximum sound output). The loudness was controlled using a step function (FIG. 8) that highlights when the error increases from a specific error region (white, green, green and red) to another.

Each sound source played a sinusoid signal with frequency Sf, phase Sp, duration Sd and a sleep interval between each tone Ssleep.

Ssleep was proportionally to the distance to reach the target. Being maxSleep and minSleep the maximum and minimum allowable sleep intervals, respectively, and $max_{dist}$ and $min_{dist}$ the maximum and minimum affecting distances, respectively, Ssleep was calculated according to Equation 4.

$$Ssleep = m * dist2target + minSleep \quad \text{Equation 4}$$

$$\text{Where } m = \frac{maxSleep - minSleep}{max\_dist - min\_dist}.$$

The following pertains to a second sound strategy—SS2. Same strategy as SS1, but now instead of not playing any sound when the needle is following the correct path (with an accuracy less $T_{err}$ mm), a sound with distinct frequency $S_2f$ is playing by all sound sources.

The following pertains to a third sound strategy—SS3. From literature, it is known that horizontal and vertical sounds are well discriminated, but it is more difficult to differentiate between front and back sounds. Efficiencies of about 50% are commonly reported [13].

Due to this shortcomings, this third strategy tries to improve front-back resolution by adding distinguish frequency tones, where front or back sources are playing. Two frequencies were used: frequencies $Sf_{front}$ for sources placed from 0° to 180° degrees; and $Sf_{back}$ for sources placed from 181° to 359° degrees. The frequency gap is used to rapidly ascertain if the needle tip should be moved to the front or back for orientation correction. With such differences, one expects to increase the localization performance, relative to the first strategy (SS1 and SS2).

The following pertains to a fourth sound strategy—SS4. In order to improve and enhance the spatial sound resolution, SS3 was further modified by introducing an intermittent sound at the four cardinal sources. These sound sources will be playing in an alternate mode two sinusoid waves: one with the parameters discussed at SS1 (Sf, Sp, Ssleep and Sd) and another with distinct frequency $S_4f$ and duration $S_4d$.

For all strategies, when the needle tip reaches the target, a message sound is generated (e.g. "Target Achieved"). Here, the surgeon must analyze the ureterenoscope video to inspect if the needle is near the target.

The following pertains to 3D vibrotactile feedback. In addition to the NeedleView and 3D sound, this work also explored vibrotactile sensation for needle guidance. Due to the desirable site of the head for providing feedback [14], one can chose to manufacture a headband with multiple actuators that vibrate according to the needle spatial errors with regards to the punctured target.

Different actuators are commercially available with particular technical specifications, mainly in terms of vibration intensity and size. Miniature loudspeakers, electromagnetic alarm buzzers and coin motors are routinely used.

When compared to other solutions, coin motors offers low cost, small size, low voltage and reduced noise devices, being used in routinely devices, e.g., mobile phones. Therefore, coin vibration actuators 308-100 Pico Vibe were used to deliver this kind of feedback. Table 4 show important actuator manufacturer specifications.

TABLE 4

308-100 Pico Vibe operation characteristics.

| Characteristic | Value |
| --- | --- |
| Diameter | 8 mm |
| Height | 3.4 mm |
| Typical Normalized Amplitude | 0.7 G |
| Rated Operating Voltage | 3V DC |
| Rated Vibration Speed | 12000 |
| Operating Current | 70 mA |
| Vibration efficiency | 3.2 g/W |
| Noise output | 50 dB |
| Typical Lag Time | 51 ms |
| Typical Rise Time | 77 ms |
| Typical Stop Time | 65 ms |

Based on a literature research [14], 8 motors were chosen and placed at the 8 cardinal points (equally placed around the head).

Four control strategies were implemented and tested. Each strategy is similar to the ones already described for the 3D sound interface (SS1, SS2, SS3 and SS4), but now a coin motor will vibrate instead of playing a sound source.

The sound loudness, Ssleep and distance to the target are now transmitted from the KidneyNav to the Arduino Uno platform wirelessly via a Bluetooth® connection. The Arduino, based on the Atmega328P microcontroller, is responsible for interpreting and processing the received information and activating/deactivating the respective actuators.

The sound loudness (values from 0 to 1) is used to control the vibration intensity Vi, as a percentage of the maximum possible vibration. The vibration sensation is achieved by individually controlling the supply voltage using a square wave signal generated by pulse width modulation (PWM).

Each motor was further connected to a 3.3 V pin at the Arduino. A diode was reversely connected to the motor to protect the microcontroller against voltage spikes. 8 transistors 2N2222 were used to assure high/low current outputs, to activate/deactivate each motor.

The following pertains to experiments. Different experiments were performed in order to evaluate the accuracy and acuity of each interface in an individual or combined way.

The following pertains to sound parameter settings. The sound parameters, such as frequency and duration were found empirically by individually playing and adjusting each source parameters with manual control. To this extent 16 participants listened sounds that were created with sinusoids which frequency vary from 300 Hz to 1200 Hz. In the end, they indicate the frequency that they were most comfortable with. Based on such results, one found that the preferred values for the first and second sound strategies (SS1 and SS2) were:

Sf=700 Hz;
Sp=0;
Sd=50 ms;
$S_2$f=950 Hz or 400 Hz;
maxSleep=800 ms;
minSleep=50 ms;
$max_{dist}$=150;
$min_{dist}$=0;

When evaluating the SS3 strategy, one found that front and back sounds can be well discriminated when $Sf_{front}$=690 Hz while $Sf_{back}$=490 Hz.

Finally, a sinusoidal sound, with $S_4$f=1200 Hz and $S_4$d=25 ms, was introduced when testing the SS4. Moreover, the frequency of the sources with positions at the most left, right, up and down were changed to 650 Hz, 650 Hz, 730 Hz and 460 Hz, respectively. The other sources remained the same $Sf_{front}$ and $Sf_{back}$ frequencies.

One found that the target can be reached accurately when $T_{err}$=2 mm. SS2 was discarded for testing because all users prefer the SS1 approach.

It should be highlighted that the user can manually control the headphones volume.

The following pertains to localization accuracy test. A set of localization experiments were firstly performed to determine whether a person is able to perceive the direction of random sources or vibration stimulus.

An audio stimuli was presented to the listener with Razer Tiamat 7.1 headphones. This headphones have 10 discrete drivers (5 for each ear) composed by neodymium magnets with 30 mm of diameter and a frequency response between 20 Hz and 20.000 Hz. They were connected to a PC via a 7.1 Surround Sound-enabled Sound Card.

On the other hand, the developed headband was used to create a vibrotactile feedback.

Before any experiment, a brief demonstration was given to each participant and they were allowed to test any sensorial feedback up to 2 minutes, so that they become comfortable and familiarized with the system.

During either audio or vibration experiments, each time the user was ready, a sound or a vibration actuator was activated randomly from a set of possible locations at the same distance from the listener.

The chosen strategy for starting the experiment was also determined randomly.

Each sound strategy (SS1, SS3 and SS4) was tested for all the three spatial configurations. In contrast, the vibrotactile feedback was tested in a single distribution. Each exercise was repeated 16 times.

The users had up to 2 seconds to report the location of the perceived sound or vibration, by marking the perceived location in a printed sheet.

In total 31 volunteers participated: 26 medical students and 5 surgeon doctors. During experiments, they had no feedback about the correctness of their answers.

The aim of this test was to select the best audio spatial configuration, sound strategy and finally compare audio against vibration as possible feedback systems.

The following pertains to phantom test. Despite of the accuracy of detecting single vibration or audio sources it is important to test the efficiency of all interfaces for needle guidance. To this extent, a phantom study was performed to test and evaluate the most valuable feedback interface. The following configurations were tested in a phantom box:
3D view
NeedleView
Audio
Vibration
3D view+NeedleView
Audio+NeedleView+3D view
Vibration+NeedleView+3D view The phantom box was made of wood without any ferromagnetic material to avoid interferences that might reduce the precision of the tracking device. A sponge material with 8 cm of thickness was used to simulate the skin, offering some resistance, low deformability and opaque texture when inserting the needle.

A small plastic arm was attached to one side of the phantom with a 10-15 cm distance from the superficial sponge material. It was used to hold the catheter sensor at different locations inside the phantom box.

When using only vibration or audio, the participants were blinded throughout all planning and puncture procedure. An audio message "target achieved" and a vibration pattern (all motors vibrate at the same time) were used to aware the participants when they reach the target (puncture success).

Puncture success was accomplished when the root mean square distance was less than 3 mm. The planning and puncture time were recorded. Needle position was then verified using a webcam showing the phantom interior. The degree of the needle tip divergence was calculated, during whole insertion procedure, by storing the root mean square distance between the real and virtual path.

The main objective was to assess whether the guidance approach increases the procedure efficiency, in terms of the duration, mean velocity, mean and maximum error.

The testing order was randomized to reduce target position-related familiarization and learning issues. Otherwise, the last guidance aspect will had an advantage over the first technique due to experience performing the puncture.

Different medical professionals with diverse expert degrees performed three times each strategy. These tests were performed by 2 different groups: naive (n=56 without any or less than 2 years of medical experience) and expert (n=15 with more than 2 years performing minimally invasive surgeries). At the beginning of each experiment the participant was allowed to practice by reorientation the needle in the air and by performing up to 2 puncture attempts. This data is not included for the statistical analysis.

Figure 9:
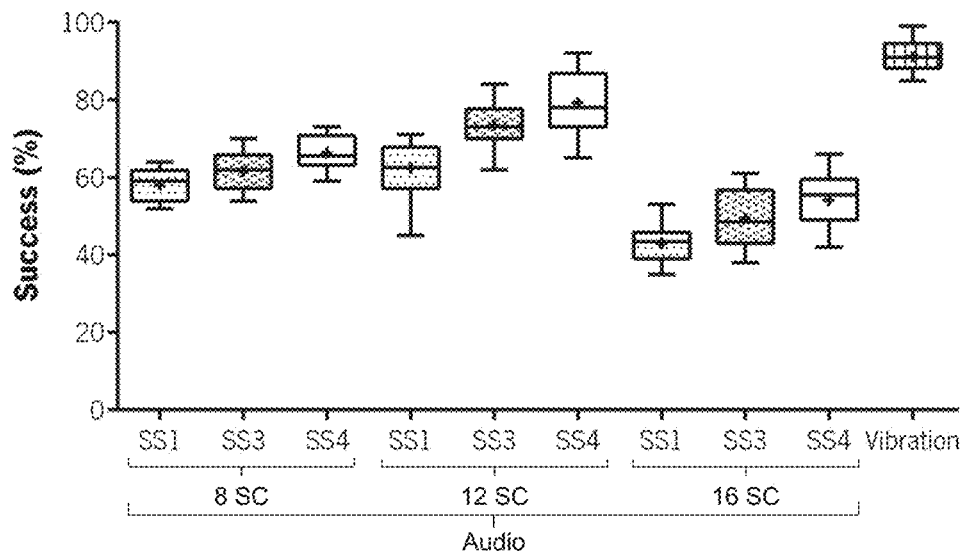
FIG. 9: Boxplots showing the percentage of times that the user accurately mark the audio or vibration source. Average values are shown by the cross symbol.
Figure 10:
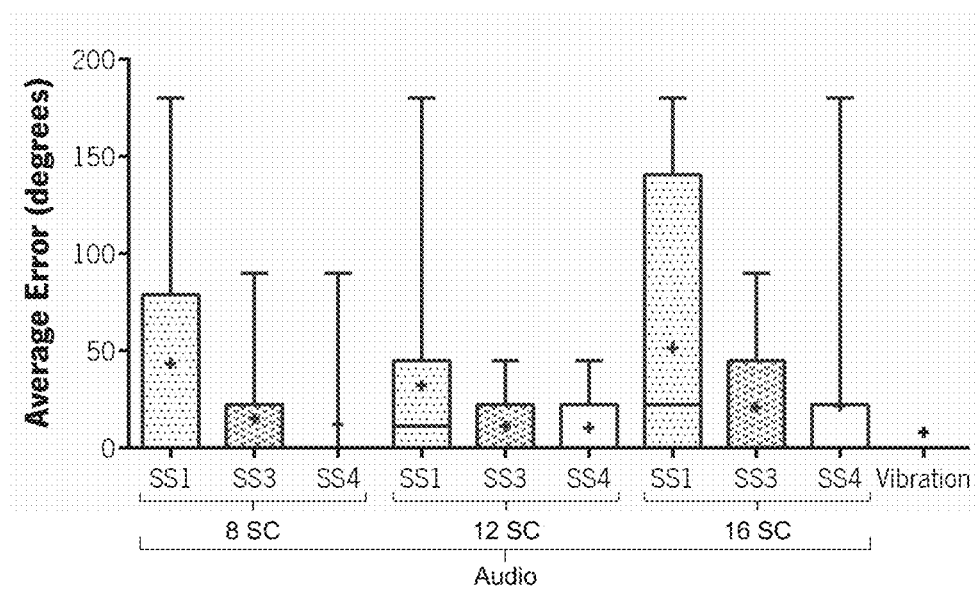
FIG. 10: Boxplots showing the angulation error when marking the audio or vibration source. Average values are shown by the cross symbol.

At the end of each test, the participant filled a questionnaire to score each approach according to the following questions:
Q0: Score each approach from 1 (most favorite) to 10 (least favorite);
Q1: Each approach based on the time needed to look to the screen from 1 (mandatory visualization throughout all procedure) and 10 (no need for visualization);
Q2: The difficulty of the procedure from 1 (very difficult) to 10 (straightforward);
Q3: The effort to familiarize with the technique from 1 (very difficult) to 10 (straightforward);

The following pertains to animal trials. The animal trials were performed as already described. In particular, the following pertains to results, further in particular of a localization accuracy test. The total duration of each experiment was about 10 minutes. FIG. 9 shows the percentage of times that the target location was correctly chosen for whole participants. FIG. 10 shows the average and standard deviation errors between the marked source and target one.

When comparing the different sound strategies and audio spatial worlds, best results were achieved when using 12 audio sources together with SS4 strategy (SS4-12SC, FIG. 6-*c*). Within this configuration, target sources were correctly chosen 79.2±8.1% of times with an average angulation error of 10.4° degrees. The worst configuration was found with SS1 strategy when using 16 audio sources (SS1-16SC—FIG. 6-b), showing an average angulation error of 51.5° degrees and an assertive percentage of 43±6.0%.

SS4 was the best sound strategy with significant statistical differences (two-way ANOVA—see attachment 1 for more detail) when compared to SS1 (p<0.0001) and SS3 (p<0.05). SS4 was followed by SS3 that also shows significant statistical differences with SS1 (p<0.01). Finally, worst results were obtained with SS1. Regarding the audio world configuration, 12SC was the best one with significant statistical differences when compared to 8SC (p<0.0001) and 16SC (p<0.0001). It was followed by 8SC with also significant statistical differences with 16SC (p<0.0001). Finally, worst results were obtained with SS1.

When listening the various sources configured with SS1, the user can easily separate left from right. However, only 62% of times he was able to identify if the sound is created at the front or back sources, creating high standard deviations between users (FIG. 10).

From the boxplot analysis (FIG. 10), more than 75% of participants did not show angulation errors when using the SS4-8SC and the vibration feedback.

By introducing $Sf_{front}$ and $Sf_{back}$ in SS3 and SS4 strategies, the user was able to improve its ability of detecting front or back sound to 87% of times.

By adding $S_4f$ and $S_4d$ to SS4, the user was able to accurately and promptly distinguish the sources placed at the four cardinal points (0°, 90°, 180° and 270°) when compared to SS1 or SS3 (71% vs. 90.5%).

Finally, vibration results were the best ones. The participants can easily and accurately identify vibration sources 91.1±3.6% of times with an average angulation error of 8.0° degrees. Significant statistical differences (p<0.0001) were found when compared to the best audio configuration (SS4-12SC).

Figure 11:
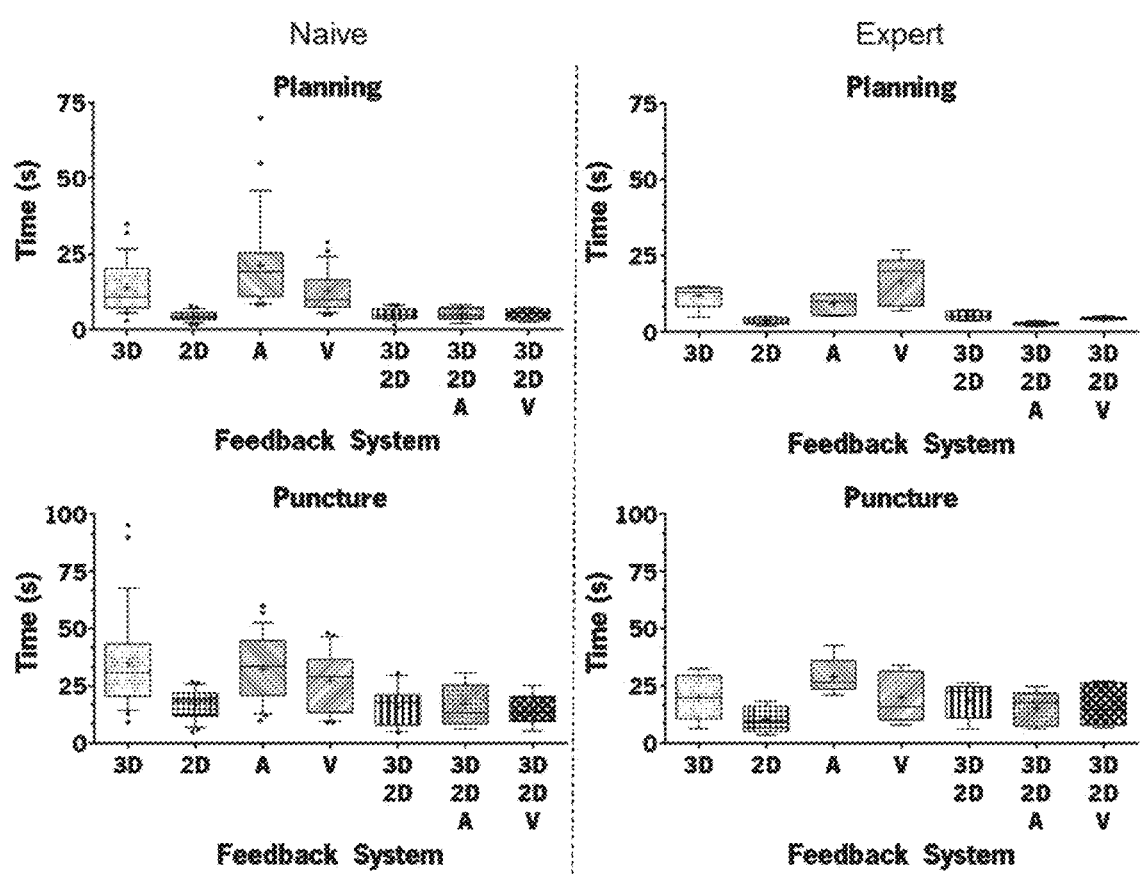
FIG. 11: Time needed for planning and puncturing for whole elements of the naive and expert group: 3D=3D View; 2D=NeedleView; A=Audio; V=Vibration; 3D/2D=3D view+NeedleView; 3D/2D/A=3D view+NeedleView+Audio; 3D/2D/V=3D view+NeedleView+Vibration.

The following pertains to phantom test. In terms of the phantom test, every subject reached the correct target in their first attempt. FIG. 11 shows the average time for planning and puncturing in both naive and expert groups. Clearly, NeedleView alone or combined with any other modalities was the fastest strategy for planning or puncturing.

On the other hand, audio or vibration alone were the ones that took longer times.

Planning significant differences between naive and expert groups were only found when using audio feedback (p<0.01). Puncture significant differences between both groups were found when inserting the needle under 3D view (p<0.05). 3D, audio and vibration are the methodologies where participants show quite range of times, especially for planning. In the naive group, planning time was minor when using the NeedleView alone (average value of 4.5±1.5 s). Higher times were achieved using the Audio feedback (21.3±15.1 s). In terms of the puncture step, best results were achieved using "3D view+NeedleView+Vibration" with an average value of 14.7±8.5 s. Surprisingly, longer puncture results were achieved with the 3D view with an average time of 34.8±21.0 s.

FIG. 12 shows multiple comparisons between all guidance strategies. Statistical analysis show that all new interfaces influenced positively the procedure performance when comparing to only the 3D views presented previously.

In the expert group, planning time was minor when using "3D view+NeedleView+Audio" with an average value of 2.7±0.6 s.

Higher times were achieved using the Vibration (16.8±8.1 s). With respect for the puncture step, best results were achieved when using "3D view+NeedleView+Audio" with an average value of 15.2±7.7 s. Longer times were needed when using the Audio feedback with an average value of 29.1±8.0 s.

The time needed for planning and puncturing is very promising, existing no statistical differences when comparing experts to naive participants in most of guidance strategies.

Figure 13:
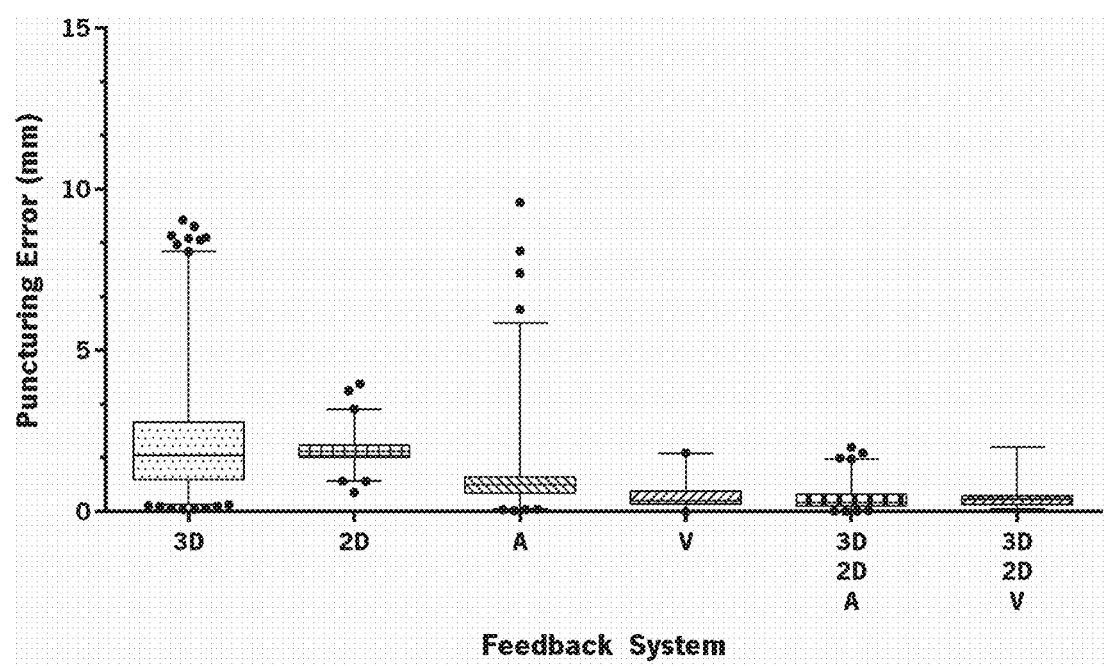
FIG. 13: Boxplots of the errors from the preferred trajectory, according to the profiles shown in FIG. 18: 3D=3D View; 2D=NeedleView; A=Audio; V=Vibration; 3D/2D/A=3D view+NeedleView+Audio; 3D/2D/V=3D view+NeedleView+Vibration.
Figure 14:
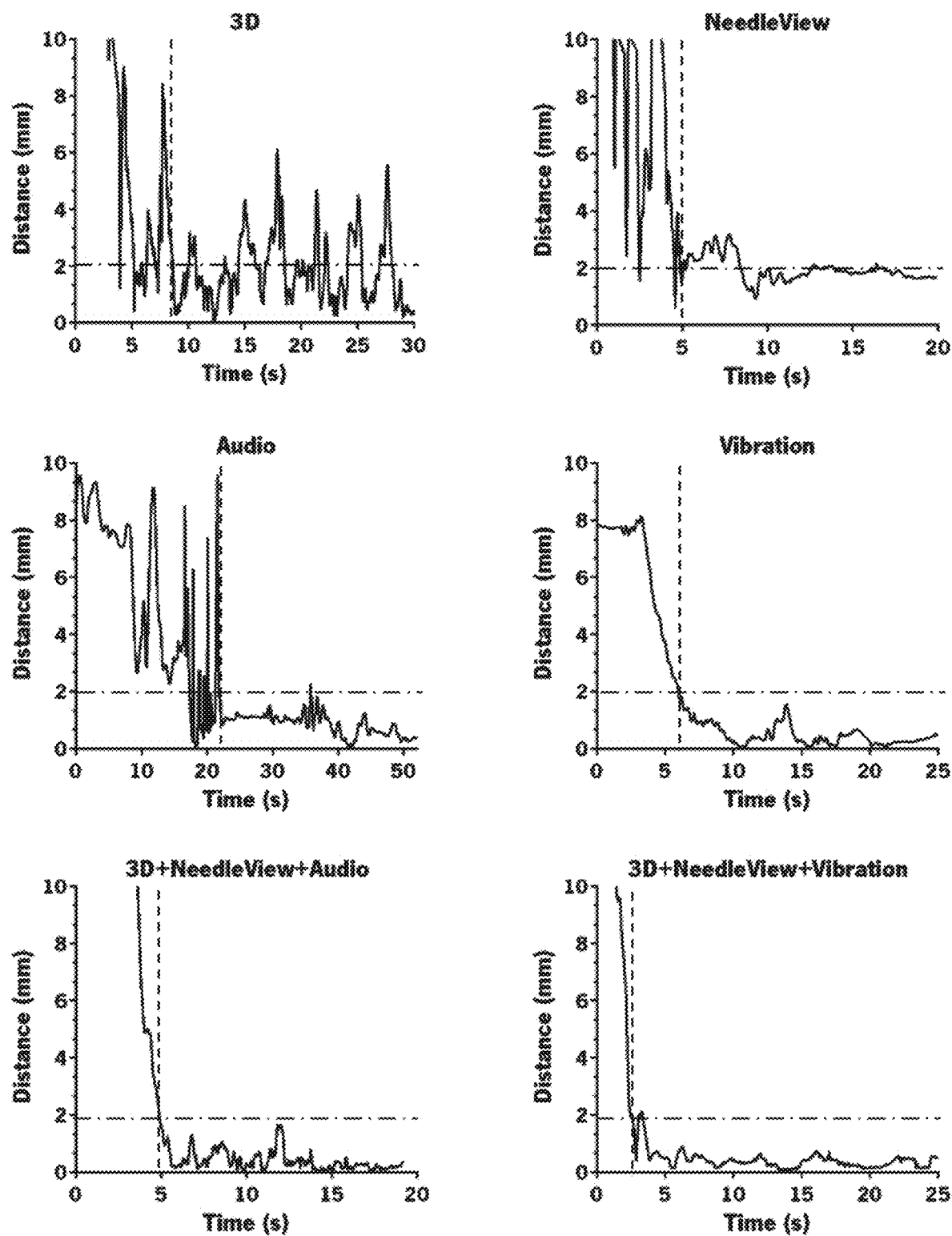
FIG. 14: Error profile deviations from the preferred trajectory when planning or puncturing according to different guidance strategies. The vertical line indicate the end of the planning procedure.
Figure 18:
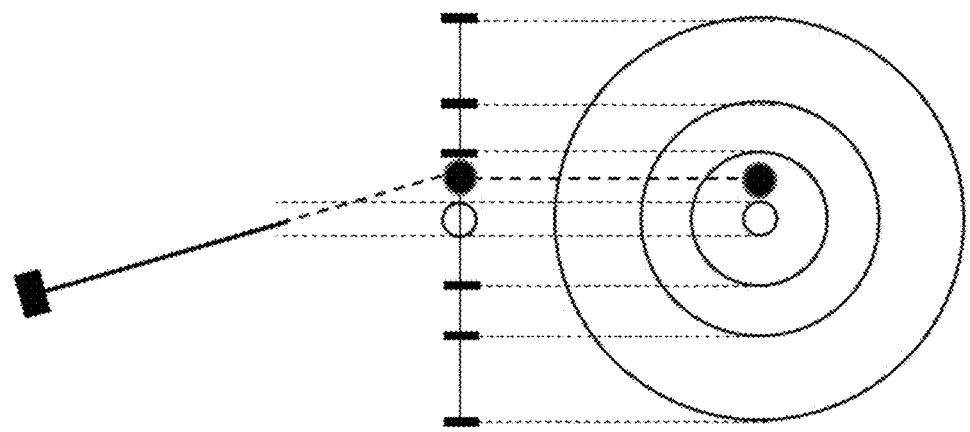
FIG. 18: Target depiction with 4 concentric rings and projection of a line coincident with the surgical needle catheter onto said target which, for illustration purposes, has not been represented perpendicular to the orientation of the surgical needle catheter.

FIG. 13 and FIG. 14 give an overview about common puncture profiles when inserting the needle with different feedbacks. As represented, using only the 3D view it was difficult to maintain the needle tip inside the 2 mm margin (white circle at the NeedleView). Errors were minimal when using "3D view+NeedleView"+"Audio" or "Vibration", because an audio or vibrotactile alert was generated each time the user increases this error. Similar errors during puncture were found when using the audio or vibration standalone, but with higher planning and puncture times. See also FIG. 18 with a target depiction with 4 concentric rings and projection of a line coincident with the surgical needle catheter onto said target which, for illustration purposes, has not been represented perpendicular to the orientation of the surgical needle catheter.

Audio and vibration feedback seemed to precisely inform the user to keep the needle correctly aligned with the target.

All participants considered that audio or vibration feedback gives less confidence than the NeedleView, but suggested that can improve the PRA procedure. Although impractical in a real situation, results reveal that the target can be reached without spending any time looking on the screen.

The step function to control the audio loudness was easy to understand for whole users. Although one tested also an exponential function (Equation 5), this option was never preferred.

$$\text{loudness} = 0.0326 e^{0.0799 \cdot err} \qquad \text{Equation 5}$$

The audio feedback combined with the NeedleView provided good directional feedback during all the procedures. This interface was the preferred and simplest one without needing any training before usage. In the presence of the NeedleView, the 3D view was frequently ignored and the audio or vibrotactile were mainly used as a warning system than a guiding one.

Table 5 shows the questionnaire for questions Q0, Q1, Q2 and Q3 (see experiments above).

TABLE 5

Questionnaire results when evaluating the different guidance approaches.

| Questions | 3D | NeedleView | Audio | Vibration | 3D + NeedleView | 3D + NeedleView + Audio | 3D + NeedleView + Vibration |
|---|---|---|---|---|---|---|---|
| Q0 | 6.25 ± 0.96 | 9.2 ± 0.7 | 5.3 ± 1.2 | 5.9 ± 1.1 | 8.8 ± 1.6 | 8.7 ± 0.7 | 6.3 ± 2.1 |
| Q1 | 1 | 1 | 10 | 10 | 1 | 5.4 ± 1.2 | 5.2 ± 1.5 |

TABLE 5-continued

Questionnaire results when evaluating the different guidance approaches.

| Questions | 3D | NeedleView | Audio | Vibration | 3D + NeedleView | 3D + NeedleView + Audio | 3D + NeedleView + Vibration |
|---|---|---|---|---|---|---|---|
| Q2 | 3.8 ± 2.3 | 10 | 2.9 ± 1.1 | 5.5 ± 0.7 | 9.5 ± 0.5 | 9.6 ± 0.5 | 9.5 ± 0.5 |
| Q3 | 4.3 ± 1.9 | 10 | 2.5 ± 0.5 | 5.7 ± 1.4 | 9.1 ± 1.1 | 8.9 ± 1.2 | 8.7 ± 1.5 |

The NeedleView followed by the "3D+NeedleView" and "3D+NeedleView+Audio" were the three most favorite methods according to Q0.

Whole users score Audio and Vibration in Q1 with 10, because they were blindfolded when performing the procedure. In contrast, visual modalities were scored with 1. Hybrid modalities that combines Visual and Audio/Vibration feedback were scored with similar values.

Regarding the question Q2, audio feedback, followed by the 3D screen, were the most difficult techniques. The easier ones were the NeedleView alone or combined with any other feedback.

Finally, Audio feedback was the most difficult technique with the highest learning curves. The NeedleView was the easiest and straightforward one, with no need for training.

Figure 15:
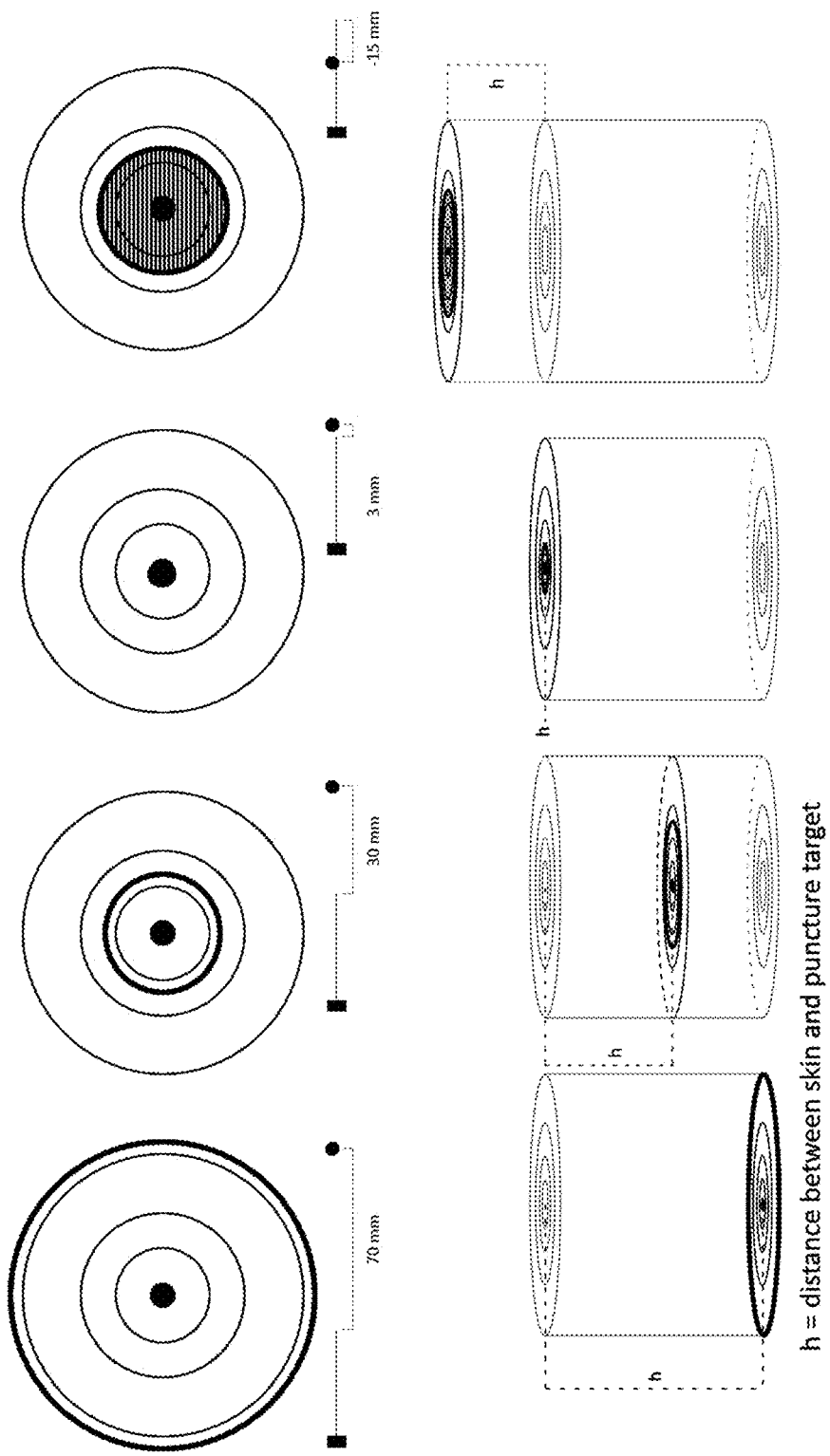
FIG. 15: Representation of the visual guidance interface while the needle approaches (or even goes beyond) the intended target for distances of: 70 mm to the target, 30 mm to the target, 3 mm to the target and 15 mm beyond the target; using a ring concentric with the target, whose diameter varies directly (e.g. proportionally) with the distance to the target and which changes (e.g. in color, fill-in, thickness) if the distance is negative (i.e. beyond the target).

The following pertains to animal trials. Eight surgeons have participated in this experiment. In order to not sacrifice many animals, surgeons start this experiment by choosing three guidance approaches. "NeedleView+3D view", "Audio alone" and "NeedleView+3D view+Audio" were the selected ones. A surgical setup is represented in FIG. 15.

Three pigs were used for this experiment. Six successful tracts to the middle of ureter were accomplished. Each ureter was punctured up to 4 times in different regions.

Due to animal's small anatomy, it was only possible to place the ureterenoscope into a kidney calyx in two pigs. Therefore, statistical analysis was only performed for the ureter experiments.

Results are in accordance with results already presented. 100% success rates were reached with only one attempt for almost all cases.

Figure 16:
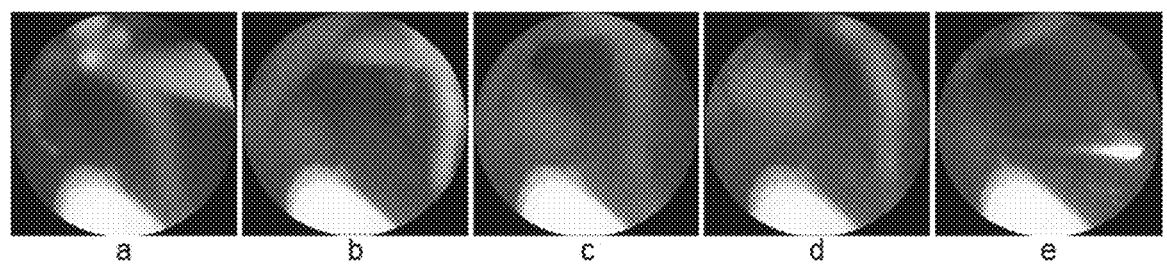
FIG. 16: Photographic illustration of the needle trying to puncture.

The time needed to see the needle tip in the ureter skin (FIG. 16-a to -d) was some seconds, but the time needle to perforate the ureter skin (FIG. 16-e) was more than 1 minute. The problem is that the ureter slipped and moved away when the needle was trying to perforate.

Figure 17:
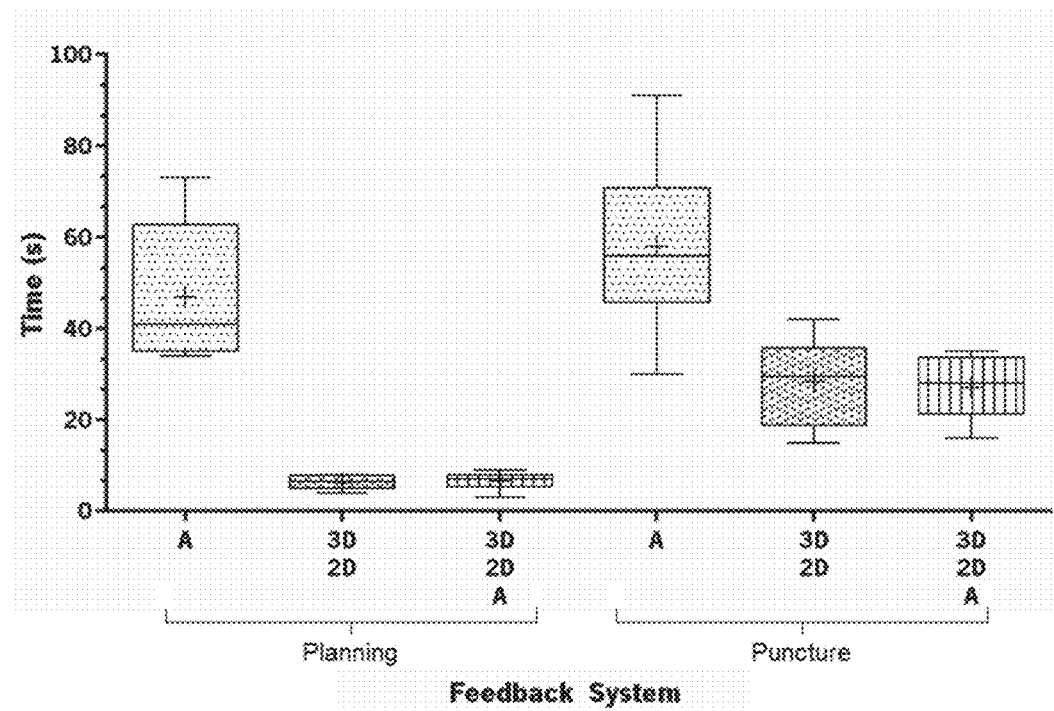
FIG. 17: Boxplots of the average times for planning and puncturing in the animal trial.

FIG. 17 presents the average times for planning and puncturing until the needle tip is visualized in the uretereno-scope camera.

Results are in accordance with the ones described with the phantom test. Longer times were obtained when performing the experiment with audio alone. Statistically significant differences were found when comparing the audio with any of the other two interfaces for surgical planning (p<0.0001) and puncturing (p<0.001).

No significant differences were found when comparing the "NeedleView+3D view" and "NeedleView+3D view+Audio". But as already described in the phantom test, that audio feedback helped the surgeon keeping the correct path with minor deviations (FIG. 14).

No major problems were found during the experiments and the most time-consuming. One attempt was needed for all surgeons.

The following pertains to further discussion. Although the KidneyNav framework already allowed surgeons to comprehend the volumetric data of the collecting system and to follow a 3D path, now one explores the possibility of adding additional feedback, by recurring to the hearing and touch senses.

It was tested multiple interfaces where audio and vibrotactile senses were combined with visual information to provide and improve insight into complex PRA trajectories. These new ways of feedback intended not to replace visual guidance, but complement the surgeon interaction with the needle, being able to anticipate any movement even without looking to a monitor.

With this multi-sensorial interface, the surgeon must place the needle at the skin surface, align with respect to the target, and finally he should puncture the kidney according to this approved angle. When the needle is being inserted from an incorrect angle, it will miss the anatomic target which error is dependent on the angulation error. This error (originated at possible needle deflection, soft tissue displacements and human tremors) can be tracked in real-time using the 3D EMT sensors at the needle and catheter tips and used to generate a set of visual, audio or vibration signals.

The previously framework, based in a 3D view, requires some learning training. Results show that by using this view, is was not possible to precisely and easily follow a pre-computed trajectory with minimal deviations from the correct path. Regardless the user experience, he can easily misunderstood the 3D information, increasing the probability of high errors.

By using the NeedleView, the user was able to automatically and intuitively classify the error as safe and dangerous. No training was required within this interface, being a ready-to-use approach. Experimental results show that NeedleView worked reasonably well for all puncture orientations being the fastest and preferred guidance aspect.

The headphones produces different spatialized sound signals relating the position of the needle with the target. Different sound frequencies were tested to create accepted tones for all users. If the needle is corrected aligned no sound was generated, avoiding possible annoyance and distractions.

Other works have reported different angulation errors around the head using headphones: 22.3°, 26°, 34.2° [13] and 22.2°. When compared to these works, results show reduced angulation errors when using the SS4 sound strategy with 12 source sounds (75% of participants show errors below 20°). The poorest scenario was shown at SS1-16SC due to the inability to clearly distinguish from front and back sounds, as well sources separated from small angles.

Although it provided limited spatial information, 3D audio feedback was enough to accurately guide the surgeons without never looking to the screen (in phantom test and animal trial). By using different audio intensities and pitches, it was possible to improve the feedback about the amount and direction of the actual deviation from the preferred trajectory.

As already reported, error angles are higher for headphones than for loudspeakers. Although surrounding loudspeakers will have better sound spatial accuracy, is unpractical to implement inside an operating room, due to all the medical armamentarium. Moreover, since the listener head must be centered with the sound system, 7.1 headphones presented a preferred solution to deal with these problems.

When studying the effect of vibration for guidance, results show that the source motors can be correctly identified with percentages higher than 90% for an 8-site configuration. Our results are in accordance with a recently described work [14], that tests the efficacy of providing vibration feedback using a headband holding 12 coin-type motors.

Although vibration was easily to understand and learn than audio, often users prefer the audio feedback combined with the NeedleView plus Audio (Table 5).

When using only audio or vibration feedback alone, the average time needed for planning or puncturing was significantly superior when compared to the NeedlleView. But when combined, this feedback helped to follow the pre-planned trajectory with minor deviations (FIG. 14). If correctly used, the disclosure exhibited potential to decrease cognitive load and alert the surgeon when the needle is moving away from the accurate path without the need to continuously interpret analyze any guidance monitor. Now, the surgeon may devote more attention to the actual needle insertion and patient conditions.

The term "comprising" whenever used in this document is intended to indicate the presence of stated features, integers, steps, components, but not to preclude the presence or addition of one or more other features, integers, steps, components or groups thereof.

Flow diagrams of particular embodiments of the presently disclosed methods are depicted in figures. The flow diagrams illustrate the functional information one of ordinary skill in the art requires to perform said methods required in accordance with the present disclosure.

It will be appreciated by those of ordinary skill in the art that unless otherwise indicated herein, the particular sequence of steps described is illustrative only and can be varied without departing from the disclosure. Thus, unless otherwise stated the steps described are so unordered meaning that, when possible, the steps can be performed in any convenient or desirable order.

It is to be appreciated that certain embodiments of the disclosure as described herein may be incorporated as code (e.g., a software algorithm or program) residing in firmware and/or on computer useable medium having control logic for enabling execution on a computer system having a computer processor, such as any of the servers described herein. Such a computer system typically includes memory storage configured to provide output from execution of the code which configures a processor in accordance with the execution. The code can be arranged as firmware or software, and can be organized as a set of modules, including the various modules and algorithms described herein, such as discrete code modules, function calls, procedure calls or objects in an object-oriented programming environment. If implemented using modules, the code can comprise a single module or a plurality of modules that operate in cooperation with one another to configure the machine in which it is executed to perform the associated functions, as described herein.

The disclosure should not be seen in any way restricted to the embodiments described and a person with ordinary skill in the art will foresee many possibilities to modifications thereof. The above described embodiments are combinable. The following claims further set out particular embodiments of the disclosure.

What is claimed is:

1. A guidance system configured to dynamically guide a surgical needle catheter for a patient comprising:
   an electromagnetic (EM) catheter configured to be inserted into the patient and for defining a desired location to be reached by the surgical needle catheter;
   an electromagnetic tracker configured to track a location and orientation of the surgical needle catheter and of a location of a tip of the electromagnetic catheter; and
   an electronic data processor arranged for:
      displaying a 2D concentric-ring target, wherein said target is on a plane intersecting the tip of the electromagnetic catheter and the plane being perpendicular to the orientation of the surgical needle catheter;
      continuously displaying a projection, orthogonal to the plane, of a line onto said 2D concentric-ring target, the line being coincident with the surgical needle catheter, wherein the projection of the line is displayed at a distance from a center of the 2D concentric-ring target when the surgical needle catheter is not pointed towards the electromagnetic catheter, and wherein the projection of the line is displayed at the center of the 2D concentric-ring target when the surgical needle catheter is pointed towards the electromagnetic catheter; and
      continuously displaying a plurality of concentric rings centered around the tip of the electromagnetic catheter.

2. The guidance system according to claim 1, wherein said concentric rings comprise an inner ring corresponding to a predetermined surgically acceptable region for the surgical needle catheter.

3. The guidance system according to claim 2, wherein said inner ring is centered around the tip of the electromagnetic catheter and has a radius of less than or equal to 1 mm, of less than or equal to 2 mm, of less than or equal to 3 mm, of less than or equal to 5 mm, of less than or equal to 8 mm, or of less than or equal to 10 mm.

4. The guidance system according to claim 1, wherein said concentric rings comprise an intermediate ring corresponding to a predetermined surgically inacceptable region for the surgical needle catheter.

5. The guidance system according to claim 4, wherein said intermediate ring is centered around the tip of the EM catheter and has a radius of less than or equal to 25 mm, of less than or equal to 30 mm, of less than or equal to 35 mm, of less than or equal to 40 mm, of less than or equal to 45 mm, or of less than or equal to 50 mm.

6. The guidance system according to claim 1, wherein said concentric rings comprise a further ring having a variable diameter depending on a spatial difference between a surgical needle catheter tip and the target.

7. The guidance system according to claim 6, wherein said further ring has a visual characteristic which is changed when the surgical needle catheter tip deviates from the target, wherein the visual characteristic is changed when the surgical needle catheter tip goes beyond the target.

8. The guidance system according to claim 7, wherein said visual characteristic is a color of the further ring, a thickness of the further ring, a fill-in of the further ring, or combinations thereof.

9. The guidance system according to claim 1, comprising a 3D sound interface configured to provide spatialized sounds according to a spatial difference between a surgical needle catheter tip and the target.

10. The guidance system according to claim 1, comprising a vibration interface configured to provide spatialized vibration feedback using vibration motors, according to a spatial difference between a surgical needle catheter tip and the target.

11. The guidance system according to claim 1, wherein the plurality of concentric rings are displayed around the target on the plane intersecting the tip of the electromagnetic catheter and being perpendicular to the orientation of the surgical needle catheter.

12. The guidance system according to claim 1, comprising the surgical needle catheter arranged for surgical operation of the organ.

13. The guidance system according to claim 12, wherein said organ is the kidney and the dynamically guiding of the surgical needle catheter is for percutaneous renal access.

14. The guidance system according to claim 1, wherein the ring target is displayed on one or more displays.

15. The guidance system according to claim 1, wherein the ring target is displayed in a virtual reality or augmented reality display.

16. A method for operating a guidance system for dynamically guiding a surgical needle catheter for a patient,
said system comprising an electromagnetic catheter configured for insertion into the patient and for defining a desired location to be reached by the surgical needle catheter; an electromagnetic tracker configured to track a location and orientation of the surgical needle catheter and of a location of a tip of the electromagnetic catheter; and an electronic data processor;
said method comprising carrying out by said electronic data processor:
displaying a 2D concentric-ring target, wherein said target is on a plane intersecting the tip of the electromagnetic catheter and the plane being perpendicular to the orientation of the surgical needle catheter;
continuously displaying, orthogonal to the plane, a projection of a line onto said 2D concentric-ring target, the line being coincident with the surgical needle catheter, wherein the projection of the line is displayed at a distance from a center of the 2D concentric-ring target when the surgical needle catheter is not pointed towards the electromagnetic catheter, and wherein the projection of the line is displayed at the center of the 2D concentric-ring target when the surgical needle catheter is pointed towards the electromagnetic catheter; and
continuously displaying a plurality of concentric rings centered around the tip of the electromagnetic catheter.

17. The method according to claim 16, wherein said concentric rings comprise an inner ring corresponding to a predetermined surgically acceptable region for the surgical needle catheter, wherein said inner ring is centered around the tip of the electromagnetic catheter and having a radius of less than or equal to 1 mm, of less than or equal to 2 mm, of less than or equal to 3 mm, of less than or equal to 5 mm, of less than or equal to 8 mm, or of less than or equal to 10 mm.

18. The method according to claim 16, wherein said concentric rings comprise an intermediate ring corresponding to a predetermined surgically inacceptable region for the surgical needle catheter, wherein said intermediate ring is centered around the tip of the electromagnetic catheter and having a radius of less than or equal to 25 mm, of less than or equal to 30 mm, of less than or equal to 35 mm, of less than or equal to 40 mm, of less than or equal to 45 mm, or of less than or equal to 50 mm.

19. The method according to claim 16, wherein said concentric rings comprise a further ring having a variable diameter depending on a spatial difference between a surgical needle catheter tip and the target.

20. The method according to claim 19, wherein said further ring has a visual characteristic which is changed when the surgical needle catheter tip deviates from the target, wherein the visual characteristic is changed when the surgical needle catheter tip goes beyond the target.

21. The method according to according claim 20, wherein said visual characteristic is the color of the further ring, the thickness of the further ring, the fill-in of the further ring, or combinations thereof.

22. The method according to claim 16, further comprising using a 3D sound interface that provides spatialized sounds according to the spatial difference between a surgical needle catheter tip and the target.

23. The method according to claim 16, further comprising using a vibration interface that provides spatialized vibration feedback using vibration motors, according to a spatial difference between surgical needle catheter tip and the target.

24. The method according to claim 16, wherein said organ is the kidney and the dynamically guiding of the surgical needle catheter is for percutaneous renal access.

25. A non-transitory computer-readable information storage media having stored thereon instructions, that when executed by a processor, perform a method in a guidance system for dynamically guiding a surgical needle catheter for a patient, said system comprising an electromagnetic catheter configured for insertion into the patient and for defining a desired location to be reached by the surgical needle catheter; an electromagnetic tracker configured to track a location and orientation of the surgical needle catheter and of a location of a tip of the electromagnetic catheter; and an electronic data processor;
said method comprising:
displaying a 2D concentric-ring target, wherein said target is on a plane intersecting the tip of the electromagnetic catheter and the plane being perpendicular to the orientation of the surgical needle catheter;
continuously displaying, orthogonal to the plane, a projection of a line onto said 2D concentric-ring target, the line being coincident with the surgical needle catheter, wherein the projection of the line is displayed at a distance from a center of the 2D concentric-ring target when the surgical needle catheter is not pointed towards the electromagnetic catheter, and wherein the projection of the line is displayed at the center of the 2D concentric-ring target when the surgical needle catheter is pointed towards the electromagnetic catheter; and
continuously displaying a plurality of concentric rings centered around the tip of the electromagnetic catheter.

26. A guidance system comprising:
an electromagnetic device configured to be inserted into a body and defining a desired target to be reached by an operative device;
an electromagnetic tracker configured to track a location and orientation of the operative device and of a location of a tip of the electromagnetic device; and
a processor and memory configured to:
display a 2D concentric-ring target on a display device, wherein said target is on a plane intersecting the tip of the electromagnetic device and the plane being perpendicular to the orientation of the operative device;
continuously display a projection, orthogonal to the plane, of a line onto said 2D concentric-ring target, the line being coincident with the operative device onto the target, wherein the projection of the line is displayed at a distance from a center of the 2D concentric-ring target when the operative device is not pointed towards the electromagnetic device, and wherein the projection of the line is displayed at the center of the 2D concentric-ring target when the operative device is pointed towards the electromagnetic device; and continuously update the display of a plurality of concentric rings centered around the tip of the electromagnetic device.

27. The guidance system of claim 26, further comprising a vibrotactile headband configured to provide tactile feedback which supplements displayed information.

28. The guidance system of claim 26, further comprising 7.1 headphones configured to provide audio feedback which supplements displayed information.

29. The guidance system of claim 26, wherein one or more of the concentric rings have a visual characteristic which is updated when the operative device deviates from the target, wherein the visual characteristic is changed when the operative device goes beyond the target.

30. The guidance system of claim 29, wherein the visual characteristic is a color of one or more of the rings, a thickness of one or more of the rings, and/or a fill-in of one or more of the rings.

* * * * *

UNITED STATES PATENT AND TRADEMARK OFFICE
CERTIFICATE OF CORRECTION

PATENT NO. : 11,944,344 B2
APPLICATION NO. : 17/032333
DATED : April 2, 2024
INVENTOR(S) : Pedro Rodrigues et al.

It is certified that error appears in the above-identified patent and that said Letters Patent is hereby corrected as shown below:

On the Title Page

Item (72) "Inventors", Column 1, Line 10, please delete "Oporto" and insert -- Porto --, therefore.

Item (72) "Inventors", Column 1, Line 12, please delete "Oporto" and insert -- Porto --, therefore.

Signed and Sealed this
Second Day of July, 2024

*Katherine Kelly Vidal*

Katherine Kelly Vidal
*Director of the United States Patent and Trademark Office*